(12) United States Patent
Leddon et al.

(10) Patent No.: US 11,577,239 B1
(45) Date of Patent: Feb. 14, 2023

(54) HANDHELD COMPOUND TESTER TO PROCESS A TABLET AND A METHOD THEREOF

(71) Applicant: JackLe LLC, Boulder, CO (US)

(72) Inventors: Jeanie C. Leddon, Boulder, CO (US); Richard L. Leddon, Boulder, CO (US); Jeffrey A Hartman, Boulder, CO (US)

(73) Assignee: JACKLE LLC, Boulder, CO (US)

( * ) Notice: Subject to any disclaimer, the term of this patent is extended or adjusted under 35 U.S.C. 154(b) by 0 days.

(21) Appl. No.: 17/862,280

(22) Filed: Jul. 11, 2022

Related U.S. Application Data

(63) Continuation of application No. 17/554,384, filed on Dec. 17, 2021.

(51) Int. Cl.
*B01L 3/00* (2006.01)
*G01N 33/94* (2006.01)

(52) U.S. Cl.
CPC ........ *B01L 3/5023* (2013.01); *G01N 33/9486* (2013.01); *B01L 2300/042* (2013.01); *B01L 2300/043* (2013.01); *B01L 2300/069* (2013.01); *B01L 2300/0825* (2013.01); *B01L 2300/0835* (2013.01); *B01L 2300/0838* (2013.01); *B01L 2300/168* (2013.01)

(58) Field of Classification Search
CPC ........................... G01N 33/9486; G01N 1/286
See application file for complete search history.

(56) References Cited

U.S. PATENT DOCUMENTS

| | | | |
|---|---|---|---|
| 5,611,995 A | 3/1997 | Zoeten et al. | |
| 6,637,683 B1 | 10/2003 | Wilbur | |
| 7,060,505 B2 | 6/2006 | Guirguis | |
| 8,388,907 B2 | 3/2013 | Gold et al. | |
| 10,119,968 B2 | 11/2018 | Lansing | |
| 2008/0118397 A1 | 5/2008 | Slowey et al. | |
| 2009/0072059 A1 | 3/2009 | Bell et al. | |

(Continued)

FOREIGN PATENT DOCUMENTS

| | | |
|---|---|---|
| CN | 211382795 U | 9/2020 |
| DE | 202005018139 U1 | 1/2006 |

(Continued)

OTHER PUBLICATIONS

BTNX Inc., Fentanyl (FYL) Forensic Test Kit, Date: Dec. 1, 2021, Web Page. Retrieved Dec. 13, 2021 at https://www.btnx.com/HarmReduction, 18 pages.

(Continued)

*Primary Examiner* — Christopher Adam Hixson
(74) *Attorney, Agent, or Firm* — Stephen B. Katsaros; Patent Engineering, LLC

(57) ABSTRACT

In one configuration, a handheld compound tester to process and detect presence of a compound in a tablet is disclosed. The handheld compound tester may include a sampling chamber configured to receive a tablet and a lid couplable with the sampling chamber. The coupling of the lid with the sampling chamber may cause cutting of the tablet. A liquid may be added inside the sampling chamber to create a mixture with segments of the tablet. The mixture may be then received by a housing adjoining the sampling chamber. A test strip disposed within the housing, upon contacting the mixture, may be configured to indicate a presence of the compound in the mixture.

20 Claims, 27 Drawing Sheets

(56) References Cited

U.S. PATENT DOCUMENTS

| | | |
|---|---|---|
| 2011/0300531 A1 | 12/2011 | Bohannon |
| 2018/0246023 A1 | 8/2018 | Muller et al. |
| 2020/0163842 A1 | 5/2020 | Mack et al. |

FOREIGN PATENT DOCUMENTS

| | | |
|---|---|---|
| EP | 3119376 B1 | 3/2020 |
| KR | 100563762 B1 | 3/2006 |
| TW | M572234 U | 1/2019 |

OTHER PUBLICATIONS

Curasia, Curasia Pill Cutter and Splitter with Dispenser, Cuts Pills, Vitamins, Tablets, Stainless Steel Blade, Travel-Sized, Date: Jun. 18, 2021, Amazon Product Sales Page. Retrieved Dec. 13, 2021 at https://www.amazon.in/dp/B097HY6R5D.

Generic, Fentanyl Synthetic Opioid Drug Test Dip Card, Date: Nov. 12, 2019, Amazon Product Sales Page, Retrieved Dec. 13, 2021 at https://www.amazon.com.au/Fentanyl-Synthetic-Opioid-Drug-Test/dp/B01J8PWEWY, 3 pages.

Healthcave, HealthCave Tablet Cutter 4 in 1, Date: Jun. 13, 2021, Amazon India Product Sales Page, Retrieved Dec. 13, 2021 at Amazon Product Sales Page: https://www.amazon.in/HealthCave-Tablet-Cutter-Crusher-Storage/dp/B09765X1G5/ref=sr_1_1?dchild=1&&keywords=HealthCave+Tablet+Cutter+4+in+1%7CCutter%7CCrusher%7Ctablet+Storage%7CWater+Storage&&qid=1628857794&&sr=8-1, 6 pages.

Right Products, Right Products Portable Perfect Travel Partner Pill Tablet Medicine Storage Compartment Box vith Sharp Blade Cutter, Date: Apr. 18, 2018, Amazon Product Sales Page, Retrieved Dec. 13, 2021 at https://www.amazon.in/Right-Products-Portable-Medicine-Compartment/dp/B07CHYCC5V/ref-sr_1_19?crid=9Q6G2WCAZGQ6&&dchild=1&&keywords=pill+splitter&&qid=1628670463&&sprefix=pill+spl%2Caps%2C523&&sr=8-19, 5 pages.

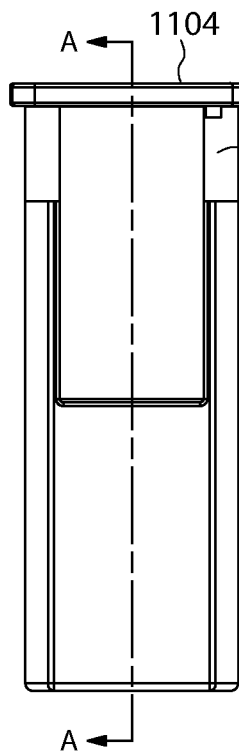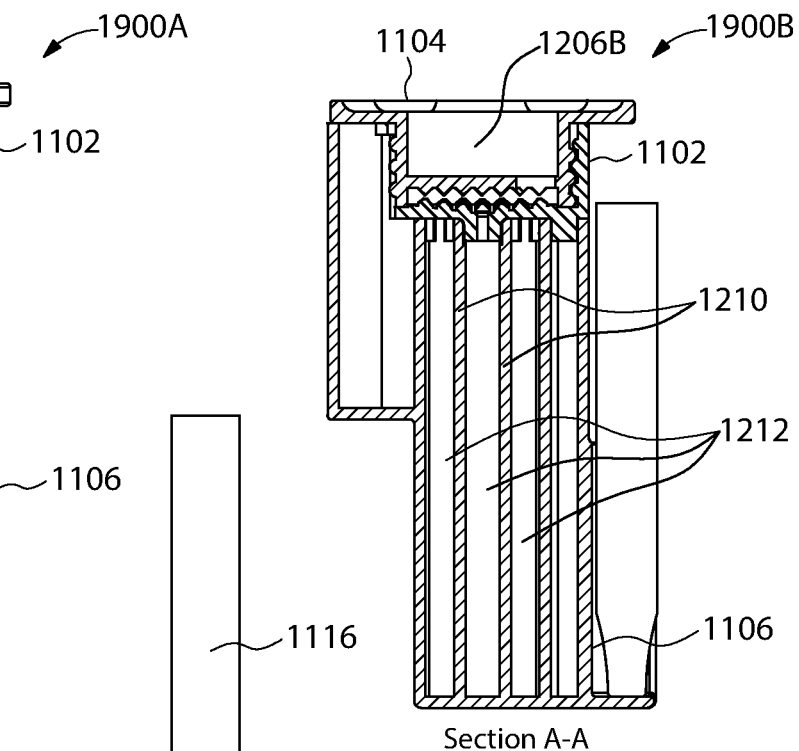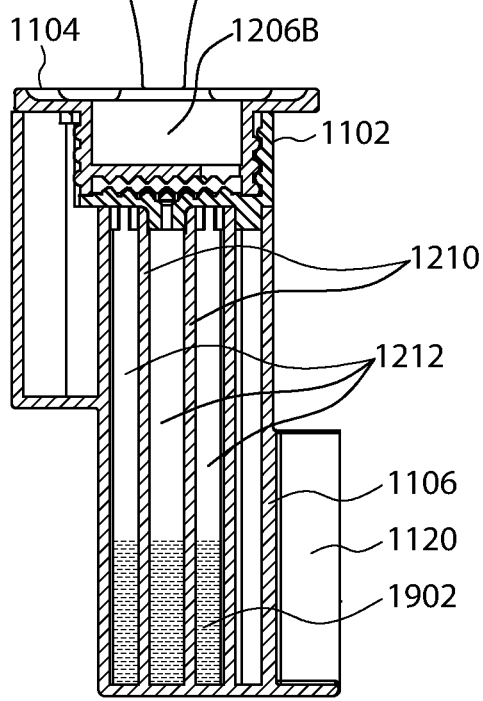
FIG. 19A
FIG. 19B
FIG. 19C

HANDHELD COMPOUND TESTER TO PROCESS A TABLET AND A METHOD THEREOF

CROSS REFERENCE TO RELATED APPLICATION

The present application claims priority to U.S. Non-Provisional patent application Ser. No. 17/554,384 entitled "HANDHELD COMPOUND TESTER TO PROCESS A TABLET AND A METHOD THEREOF", by JEANIE C. LEDDON, filed on 17 Dec. 2021. The entirety of the aforementioned application is incorporated herein by reference for all purposes.

TECHNICAL FIELD

This disclosure relates generally to a tablet testing for presence of a compound, and particularly to a handheld compound tester to process a tablet and detect presence of a compound in the tablet and methods thereof.

BACKGROUND

Drugs meant to be taken orally, for example, tablets may require testing before consumption, for various reasons. For example, when the tablet is being offered by an unknown person (e.g. during a social gathering, a concert, etc.), it may be important to check if the tablet is safe and does not include a prohibited or an unsafe ingredient. However, while there may be an urgent need to consume the tablet, there may not be adequate means to conduct the testing. This is because the testing may require the tablet to be crushed, mixing the tablet in a solvent, and lastly contacting the solvent containing the tablet with a test strip which may indicate the presence of a prohibited or unsafe ingredient in the tablet.

However, it may be a challenge to perform all the above steps, especially when the testing is to be performed at a short notice and at a remote location where arranging the testing apparatus and test components (i.e. tablet crusher, solvent, test strip) is not possible.

In short, a portable and an all-inclusive testing solution for testing safety of a drug is desired that can be easily usable for obtaining test results.

SUMMARY

A handheld compound tester is disclosed. The handheld compound tester provides a lightweight and a portable solution for testing safety of a drug, for example a drug in form of a tablet, with respect to presence of a specific compound, for example fentanyl. The handheld compound tester is portable and handy device which can be easily carried inside a pocket and is ready to use. Further, the handheld compound tester is self-contained and does not require any additional components or ingredients to conduct the testing. As such, the handheld compound tester is an ideal solution for testing a tablet when an immediate testing is required, for example during social parties where a user may want to test the tablet offered by a stranger.

The handheld compound tester is capable of cutting/crushing the tablet and includes its own supply of a liquid (e.g. water) which is required for testing. The handheld compound tester includes an exact amount of liquid required for accurate testing, and thereby eliminates the chances of inaccurate results due to use excessive or lesser amount of liquid.

Further, the handheld compound tester provides for easily viewable and interpretable results of the testing via a test strip which is provided as part of the handheld compound tester. The test strip is positioned in way that the test strip is able to contact just the right amount of the mixture (of the tablet and the liquid) for accurate test results.

Furthermore, the handheld compound tester requires only a small portion of the tablet for carrying out the testing, while the unused portion of the tablet can be retrieved post the testing. The handheld compound tester makes sure that the unused portion of the tablet is not contaminated by the liquid during testing and therefore is available for consumption if the tablet is found to be safe for use.

In one illustrative configuration, a handheld compound tester to process and detect presence of compound in a tablet is disclosed. The handheld compound tester may include a sampling chamber configured to receive a tablet. The sampling chamber may include at least one inner boundary wall and a bottom surface. The bottom surface may include a bottom hole. The handheld compound tester may further include a lid couplable with the sampling chamber. The lid may include a top side, a bottom side, and an opening across the top side and bottom side to provide a supply of a liquid into the sampling chamber. The lid may be configurable between an open position and a closed position. In the open position, the lid may be uncoupled from the sampling chamber. In the closed position, different than the open position, the lid may be coupled with the sampling chamber to thereby define an inner space along with the at least one inner boundary wall and the bottom surface. Further, the lid may be configurable in a cut position different than the open position and the closed position. In the cut position, the lid may be further configured to cut the tablet inside the sampling chamber during the transition from the open position to the closed position. The handheld compound tester may further include a housing adjoining the sampling chamber. The housing may be fluidically coupled with the sampling chamber via the bottom hole to receive a mixture of the liquid and a segment of the tablet created upon cutting of the tablet. The handheld compound tester may further include a test strip disposed within the housing. The test strip may be configured to contact the mixture, and upon contacting, the test strip may be further configured to indicate a presence of the compound in the mixture. At least a portion of the test strip may be configured to be visible to a user.

In one illustrative configuration, the housing of the handheld compound tester may include a plurality of vertical walls defining a plurality of compartments. A test compartment of the plurality of compartments may be fluidically coupled with the sampling chamber via the bottom hole to receive the mixture of the liquid and the segment of the tablet. The test strip may be disposed within the test compartment. The test compartment may be configured to receive a maximum predefined volume of the mixture. The maximum predefined volume of the mixture is to contact a maximum predefined length of the test strip from a bottom end of the test strip.

In one illustrative configuration, the housing of the handheld compound tester may further include a cut-out window located along the test compartment, such that wherein the test strip may be configured to be positioned adjacent to the cut-out window, and at least a portion of the test strip may be visible to the user via the cut-out window. In one illustrative configuration, the housing may be transparent and at least a portion of the test strip may be visible to the user via the transparent housing.

In one illustrative configuration, the handheld compound tester may further include a chute defined adjacent to the sampling chamber. The chute may be configured to receive remaining segments of the tablet created upon cutting of the tablet. Further, the at least one inner boundary wall may include a side opening, such that the chute may be configured to receive the remaining segments of the tablet via the side opening.

In one illustrative configuration, the lid may be couplable with the sampling chamber or the housing via a hinged coupling. The lid may include a partition wall projecting substantially perpendicular to the bottom side of the lid. In the closed position of the lid, the partition wall may be configured to extend over the side opening to block passage of the liquid or the mixture from the sampling chamber to chute. Further, the lid may include at least one projection projecting perpendicular to the bottom side of the lid that may be configured to contact and cut the tablet inside the sampling chamber during the transition of the lid from the open position to the closed position.

In one illustrative configuration, the bottom surface of the sampling chamber may include a plurality of spikes pointing towards the bottom side of the lid. During the transition of the lid from the open position to the closed position, the tablet may be sandwiched between the plurality of spikes and the at least one projection.

In one illustrative configuration, the lid may be couplable with the sampling chamber via a thread coupling. Further, the bottom side of the lid may include a threaded head configured to engage with a threaded portion of the sampling chamber to couple the lid with the sampling chamber in the closed position. The threaded portion of the sampling chamber may be defined along the inner boundary wall of the sampling chamber. In the closed position of the lid, the threaded head may be configured to extend over the side opening to block passage of the liquid or the mixture from the sampling chamber to chute.

In one illustrative configuration, the handheld compound tester may further include a liquid ampoule configured to store a predetermined volume of liquid. The liquid ampoule may be configured to be detachably attached to the housing. The liquid ampoule may include a dispensing head to dispense the liquid stored inside the liquid ampoule, the dispensing head being configured to fit into the opening of the lid to supply the liquid inside the sampling chamber. Further, the liquid ampoule may be squeezable, such that upon being squeezed, the liquid ampoule may be configured to supply the liquid stored inside the liquid ampoule to the sampling chamber via the dispensing head.

In one another illustrative configuration, method of processing and detecting presence of a compound in a tablet is disclosed. The method may include providing an apparatus for processing and detecting presence of the compound in the tablet. The apparatus may include a sampling chamber. The sampling chamber may further include at least one inner boundary wall and a bottom surface which may further include a bottom hole. The apparatus may further include a lid couplable with the sampling chamber. The lid may include a top side, a bottom side, and an opening to provide a supply of liquid into the sampling chamber. The lid may be configured to transition between an open position and a closed position. In the open position, the lid may be uncoupled from the sampling chamber, in the closed position, the lid may be coupled with the sampling chamber to thereby define an inner space along with the at least one inner boundary wall and the bottom surface. The apparatus may further include a housing defined vertically below the sampling chamber. The housing may be fluidically coupled with the sampling chamber via the bottom hole. The apparatus may further include a test strip disposed within the housing. The method may further include positioning the tablet inside sampling chamber, in the open position of the lid, transitioning the lid from the open position to the closed position to cut the tablet inside the sampling chamber and to obtain the closed position of the lid, and supplying the liquid to the sampling chamber to create a mixture of the liquid and a segment of the tablet created upon cutting of the tablet. Upon creation of the mixture, the mixture may be received by the housing from the sampling chamber via the bottom hole, to contact the test strip. The method may further include viewing the test strip. Upon contacting, the test strip may be configured to indicate a presence of the compound within the mixture.

In one illustrative configuration, the housing may further include a plurality of vertical walls defining a plurality of compartments. A test compartment of the plurality of compartments may be fluidically coupled with the sampling chamber via the bottom hole and configured to receive the mixture of the liquid and the segment of the tablet. The test compartment may be further configured to receive a maximum predefined volume of the mixture. The test strip may be disposed within the test compartment. The maximum predefined volume of the mixture may contact a maximum predefined length of the test strip from a bottom end of the test strip. The apparatus may further include a chute defined adjacent to the sampling chamber that is configured to receive remaining segments of the tablet created upon cutting of the tablet, via a side opening defined on the at least one inner boundary wall of the sampling chamber. The chute may include an open top face. In one illustrative configuration, the method may further include retrieving the remaining segments of the tablet from the chute via the open top face.

In one illustrative configuration, the lid may be couplable with the sampling chamber via a hinged coupling. The transitioning of the lid from the open position to the closed position may include rotating the lid about the hinged coupling. Further, the lid may include a partition wall formed on the surface of the lid and projecting substantially perpendicular to the bottom side of the lid. In the closed position of the lid, the partition wall may be configured to extend over the side opening to block passage of the liquid or the mixture from the sampling chamber to chute via the side opening.

In one illustrative configuration, the lid may be couplable with the sampling chamber via a thread coupling. The lid may include a threaded head projecting from a bottom side of the lid, and configured to engage with a threaded portion of the sampling chamber to couple the lid with the sampling chamber in the closed position. The threaded portion of the sampling chamber may be defined along the inner boundary wall of the sampling chamber. The transitioning of the lid from the open position to the closed position may include rotating the lid about an axis perpendicular to the bottom side of the lid, to couple the threaded head of the lid with the threaded portion of the sampling chamber.

In one illustrative configuration, the apparatus may further include a liquid ampoule detachably attached to the apparatus. The liquid ampoule may be configured to store a predetermined volume of liquid. The liquid ampoule may include a dispensing head configured to fit into the opening of the lid and dispense the liquid stored inside the liquid ampoule. Further, supplying the liquid to the sampling chamber may include detaching the liquid ampoule from the apparatus, fitting the dispensing head into the opening of the lid, and upon fitting, squeezing the liquid ampoule to dispense the liquid into the sampling chamber.

In one illustrative configuration, another handheld compound tester for processing a tablet is disclosed. The handheld compound tester may include a sampling chamber configured to receive a tablet. The sampling chamber may include at least one inner boundary wall which may include a side opening and a bottom surface including a bottom hole. The handheld compound tester may further include a lid couplable with the sampling chamber. The lid may include an opening to provide a supply of liquid into the sampling chamber. The lid may be configured to transition between an open position and a closed position. In the open position, the lid may be uncoupled from the sampling chamber, and in the closed position, the lid may be coupled with the sampling chamber to thereby define an inner space along with the at least one inner boundary wall and the bottom surface. The lid may be further configured to cut the tablet inside the sampling chamber during the transition from the open position to the closed position into a plurality of segments. The handheld compound tester may further include a chute defined adjacent to the sampling chamber that is configured to receive one or more of the plurality of segments of the tablet created upon cutting of the tablet, via the side opening.

In one illustrative configuration, the handheld compound tester may further include a housing configured to be attached vertically below the sampling chamber. The housing may be further configured to be fluidically coupled with the sampling chamber via the bottom hole to receive a mixture of the liquid and a segment from the plurality of segments of the tablet created upon cutting of the tablet. The handheld compound tester may further include a test strip disposed within the housing. The test strip may be configured to contact the mixture. Upon contacting, the test strip may be further configured to indicate a presence of a compound in the mixture. The test strip may be further configured to be visible to a user through the housing.

In one illustrative configuration, a method of processing a tablet is disclosed. The method may include positioning the tablet in a sampling chamber. The sampling chamber may include at least one inner boundary wall including a side opening and a bottom surface including a bottom hole. The method may further include transitioning a lid from an open position and a closed position to cut the tablet inside the sampling chamber during the transition into a plurality of segments. In the open position, the lid may be uncoupled from the sampling chamber. In the closed position, the lid may be coupled with the sampling chamber to thereby define an inner space along with the at least one inner boundary wall and the bottom surface. The lid may include an opening to provide a supply of liquid into the sampling chamber. The method may further include receiving one or more of the into a plurality of segments of the tablet created upon cutting of the tablet in a chute, via the side opening. The chute may be defined adjacent to the sampling chamber.

In one illustrative configuration, the method may further include receiving a mixture of the liquid and a segment of plurality of segments of the tablet created upon cutting of the tablet in a housing configured to be positioned vertically below the sampling chamber. The housing may be further configured to be fluidically coupled with the sampling chamber via the bottom hole. The method may further include viewing a test strip disposed within the housing. The test strip may be configured to contact the mixture. Upon contacting, the test strip may be further configured to indicate a presence of a compound in the mixture. The test strip may be configured to be visible to a user through the housing.

Further areas of applicability of the present disclosure will become apparent from the detailed description provided hereinafter. It should be understood that the detailed description and specific examples, while indicating various configuration, are intended for purposes of illustration only and are not intended to necessarily limit the scope of the disclosure.

BRIEF DESCRIPTION OF THE DRAWINGS

The accompanying figures of the drawing, which are included to provide a further understanding of general aspects of the system/method, are incorporated in and constitute a part of this specification. These illustrative aspects of the system/method, and together with the detailed description, explain the principles of the system. No attempt is made to show structural details in more detail than is necessary for a fundamental understanding of the system and various ways in which it is practiced. The following figures of the drawing include:

FIG. 19A illustrates a side view of the handheld compound tester of FIG. 11, in accordance with some configurations;

FIG. 19B illustrates a first sectional view of the handheld compound tester of FIG. 19A along a section line B-B' in a first configuration, in accordance with some configurations;

FIG. 19C illustrates a second sectional view of the handheld compound tester of FIG. 9A along the section line B-B' in a second configuration, in accordance with some configurations;

The figures illustrate ornamental designs that include extraneous features, for example, the embodiment illustrated in FIGS. 21-26 may be amended to remove features such as a liquid ampoule, a holder, a cut-out window, an opening, etc. The same broadening amendment may be applied to other embodiments such as the ornamental illustration in FIGS. 27-32.

In the appended figures, similar components and/or features may have the same numerical reference label. Further, various components of the same type may be distinguished by following the reference label with a letter. If only the first numerical reference label is used in the specification, the description is applicable to any one of the similar components and/or features having the same first numerical reference label irrespective of the suffix.

DETAILED DESCRIPTION

Illustrative configurations are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed configurations. It is intended that the following detailed description be considered as exemplary only, with the true scope and spirit being indicated by the following claims.

It is desirable to provide a lightweight and portable compound tester for testing safety of a drug, for example a tablet, with respect to presence of a specific compound in the drug. Further, it is desirable that the compound tester is self-contained and does not require any additional components or ingredients to conduct the testing. Furthermore, it is desirable that the compound tester includes the capability of cutting/crushing the tablet and further includes a supply of a liquid required for testing. Since the amount of liquid used is important for accurate testing, it may be further desirable that the compound tester provides an exact measured volume of the liquid for testing. It is further desirable that the compound tester provides for easily viewable and interpretable results. Moreover, it may be advantageous to retrieve unused portions of the tablet post the testing and avoid wastage.

Figure 1A:
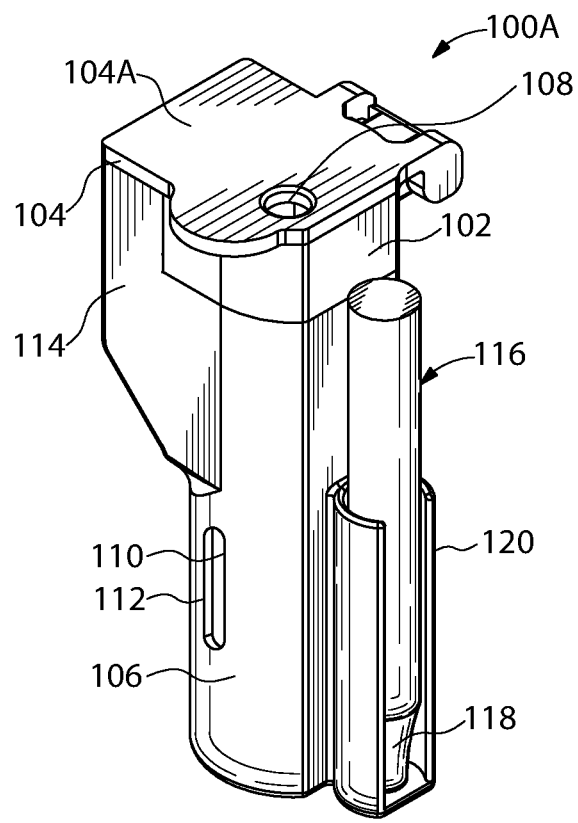
FIGS. 1A-1B illustrates perspective views of an exemplary handheld compound tester to process and detect presence of a target compound in a tablet, in a closed position of a lid, in accordance with some configurations of the present disclosure.
Figure 1B:
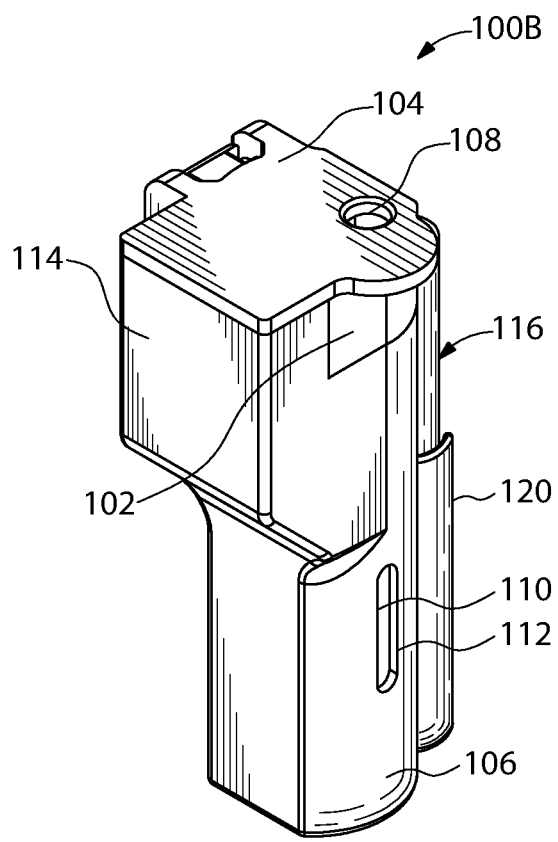

Referring now to FIGS. 1A-1B, perspective views 100A and 100B of an exemplary handheld compound tester 100 to process and detect presence of a target compound in a tablet, in a closed position of a lid, are illustrated in accordance with some configurations of the present disclosure. The handheld compound tester 100 may include a sampling chamber 102 configured to receive the tablet (not shown in FIGS. 1A-1B) that is to be tested. It should be noted that the term tablet may refer to any pharmaceutical or recreational drug in any configuration including, but not limited to, a solid (e.g. a pressed tablet), a paste, or a liquid. Further, the tablet may be of any shape and size including, but not limited to, a spherical, a disc-like, or an oval shape. The handheld compound tester 100 may further include a lid 104 couplable with the sampling chamber 102. The lid 104 may include an opening 108 to provide a supply of liquid to the sampling chamber 102. Further, the lid 104 may include a top side 104A and a bottom side (not shown in FIG. 1).

As shown in the FIGS. 1A-1B, in the closed position of the lid 104, the lid 104 may be coupled with the sampling chamber 102 to define an inner space which may receive the tablet. As will be explained in the subsequent sections of this disclosure, the lid 104 may be configured to transition between an open position and the closed position. In the open position, the lid 104 may be uncoupled from the sampling chamber 102 (as later shown in FIG. 10) As shown in FIGS. 1A-1B, in the closed position, the lid 104 may be uncoupled from the sampling chamber 102. The lid 104 may be further configurable in a cut position which may be different than the open position and the closed position. In the cut position, the lid 104 may be configured to cut the tablet inside the sampling chamber 102. In particular, during the transition from the open position to the closed position, the lid 104 may cut the tablet into multiple segments inside the sampling chamber 102. Thereafter the liquid, for example water, may be supplied to the sampling chamber 102 that may create a mixture with some of the segments of the tablet.

The handheld compound tester 100 may further include a housing 106 which may adjoin the sampling chamber 102 and may be fluidically coupled with the sampling chamber 102. The housing 106 may be configured to receive the mixture of the liquid and the segments of the tablet.

In some configurations, a test strip 110 may be disposed within the housing 106. The test strip 110 may be configured to contact the mixture received in the housing 106, and upon contacting, the test strip 110 may be further configured to indicate a presence of the target compound in the mixture and therefore in the tablet. For example, upon contacting the mixture containing the target compound, for example, fentanyl, a chemical reaction of the target compound with the test strip (for example, with a chemical provided on the test strip) may take place. This chemical reaction may cause a color change of a section of the test strip 110. However, if the mixture does not contain the target compound, no such chemical reaction or the color change of the test strip 110 may take place. An occurrence of such color change may therefore indicate presence of the target compound in the mixture and the tablet. The test strip 110 may be visible to a user through the housing 106. To this end, for example, the housing 106 may include a cut-out window 112 with the test strip 110 being positioned adjacent to the cut-out window 112. Alternately, the housing 106 itself may be transparent to allow the test strip 110 to be visible to the user but none-the-less includes an area through which the test strip 110 is visible; therefore, the term 'cut-out window' 112 is utilized in any and all configurations (e.g. an actual opening through which the test trip 110 can be seen or a transparent area).

In some configurations, the handheld compound tester 100 may further include a chute 114 adjoining the sampling chamber 102. The chute 114 may be configured to receive remaining segments of the tablet created upon cutting of the tablet. In other words, while some of the segments created upon cutting of the tablet may be directed into the housing 106 in form of the mixture with the liquid, the remaining segments may pass into the chute 114. These segments in the chute 114 are therefore not exposed to the liquid and can later be recollected by the user.

The liquid to be supplied into the sampling chamber 102 may be retrieved from a liquid ampoule 116. The liquid ampoule 116may be configured to store a predetermined volume of liquid and may be provided as detachably attached to the handheld compound tester 100, in particular detachably attached to the housing 106 via a holder 120. In some configurations, the holder 120 may be formed into the housing, i.e. manufactured along with the housing 106. Alternatively, the holder 120 may be later attached to a manufactured housing 106, for example, via gluing, welding, or using fasteners like screws, rivets, etc.

The liquid ampoule 116 may include a dispensing head 118 to dispense the liquid which is stored inside the liquid ampoule 116. The dispensing head 118 may be configured to fit into the opening 108 of the lid 104 to supply the liquid to the sampling chamber 102. In some configurations, the liquid ampoule 116 may be squeezable, such that, upon being squeezed, the liquid inside the liquid ampoule 116 is pushed out via the dispensing head 118 and supplied to the sampling chamber 102. In some alternate configurations, the liquid ampoule 116 may include a piston-cylinder assembly, such that the liquid inside the cylinder may be pushed out by pushing the piston and therefore supplied to the sampling chamber 102.

Figure 2:
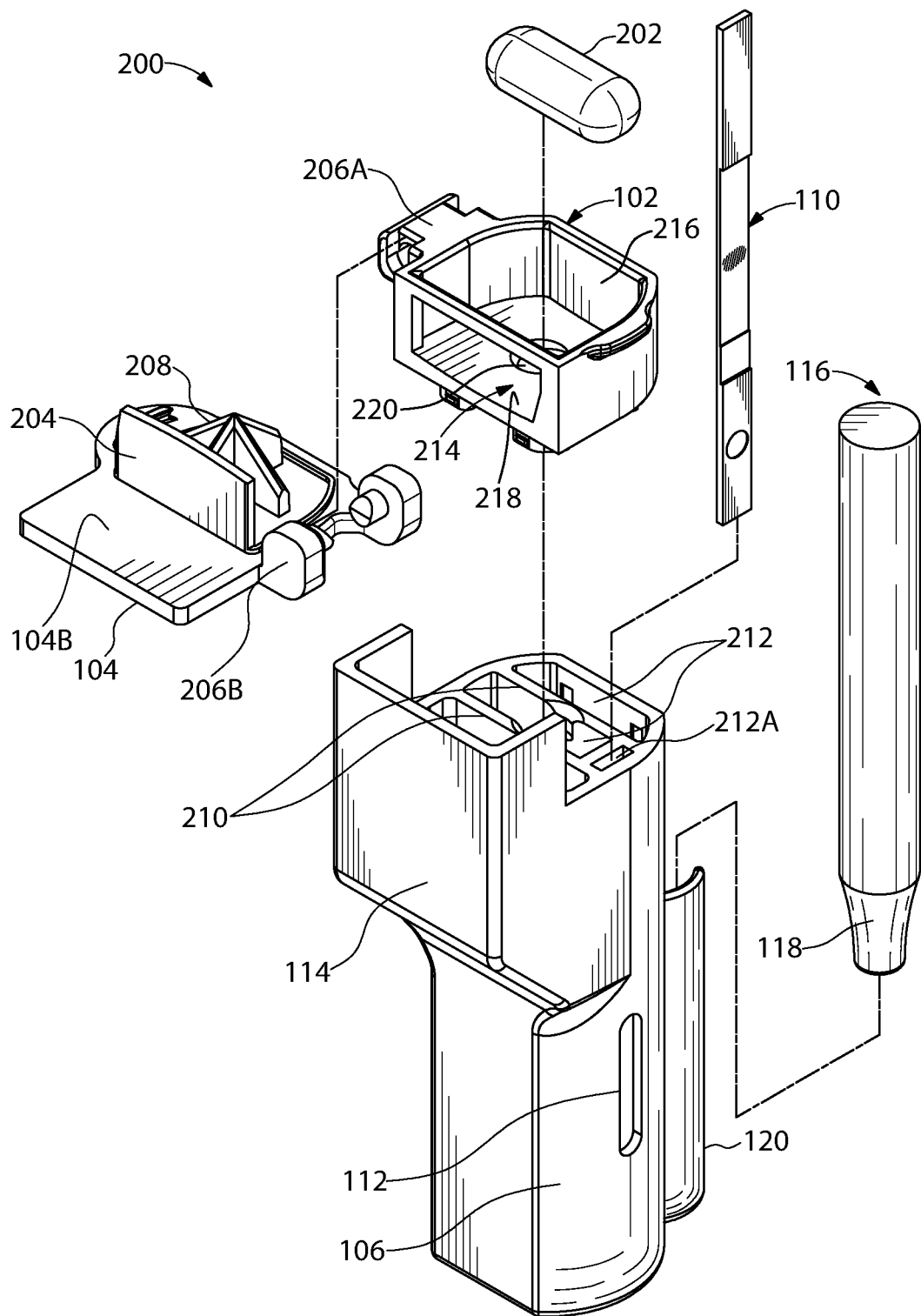
FIG. 2 illustrates an exploded view of the handheld compound tester of FIGS. 1A-1B, in accordance with some configurations.

Referring now to FIG. 2, an exploded view 200 of the handheld compound tester 100 of FIGS. 1A-1B is illustrated, in accordance with some configurations of the present disclosure. As already mentioned above, the handheld compound tester 100 may include the sampling chamber 102, the lid 104, the housing 106, the test strip 110, the chute 114, and the liquid ampoule 116.

The sampling chamber 102 may be configured to receive a tablet 202 that is to be tested. The sampling chamber 102 may include at least one inner boundary wall 216. For example, as shown in FIG. 2, the sampling chamber 102 may have a substantially square profile and therefore may include four inner boundary walls 216. The sampling chamber 102 may further include a bottom surface 218 which may further include a bottom hole 220. The sampling chamber 102 may be made of any rigid material selected from a plastic, a metal, an alloy, etc.

The lid 104 may include the top side 104A (not visible in FIG. 2) and a bottom side 104B. Further, the lid 104 may include the opening 108 (not visible in FIG. 2) across the top side 104A and bottom side 104B. This opening 108 may be used to provide a supply of liquid to the sampling chamber 102. It should be noted that the liquid may include any solvent which is configured to mix with the tablet (segments of the tablet) and further configured to allow the mixture to be tested using the test strip 110 to detect presence of the target compound inside the tablet 202. It should be further noted that the term liquid may not be interpreted to be limited to solvents in liquid state and may also include solvents in form of a powder, a paste, etc.

The lid 104 may be couplable with the sampling chamber 102. In some configurations (as shown in FIGS. 1-16), the lid 104 may be couplable with the sampling chamber 102 via a hinged coupling. To this end, the lid may include a first hinge member 206A and the sampling chamber 102 may include a second hinge member 206B. The first hinge member 206A of the lid 104 may engage with the sampling chamber 102 to thereby allow the lid to rotate about the hinged connection to transition between the open position and the closed position. The lid 104 may be made of any rigid material selected from a plastic, a metal an alloy, etc.

In some configurations, the inner boundary wall 216 of the sampling chamber 102 may include a side opening 214. As mentioned above, as the lid 104 transitions into the cut position, i.e. transitions from the open position to the closed position, the tablet 202 inside the sampling chamber 102 is cut into a plurality of segments. While some of the segments may be directed into the housing 106 in form of the mixture (along with the liquid), some of the segments may be received by the chute 114 from the sampling chamber 102 via the side opening 214. Further, the lid 104 may include a partition wall 204 which may be projecting substantially perpendicular to the bottom side 104B of the lid 104, as shown in FIG. 2. As the lid 104 transitions from the open position to the closed position, the partition wall 204 may divide the segments of the tablet 202 between two parts, i.e. segments which are passed to chute 114 and the segments which are directed into the housing 106 upon being mixed with the liquid. This is further explained in conjunction with FIGS. 3A-3B.

Figure 3A:
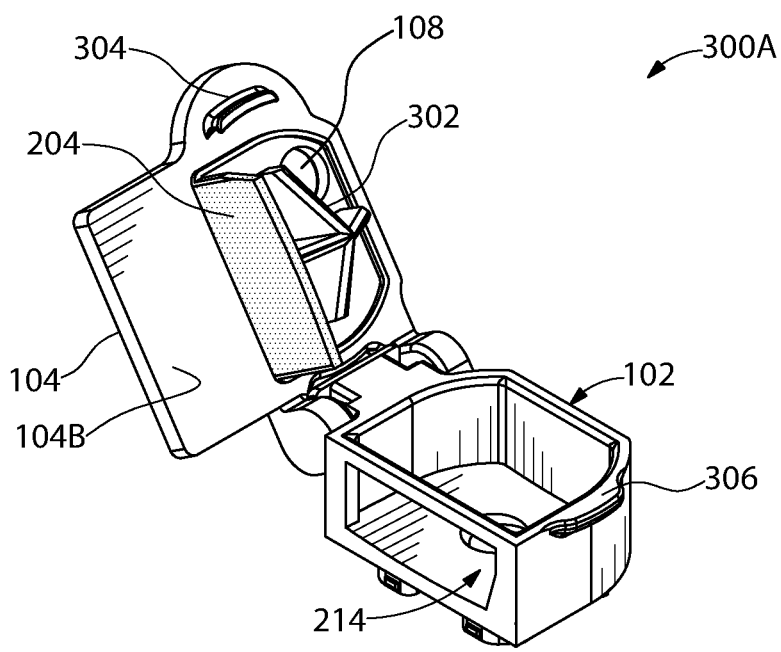
FIGS. 3A-3B illustrates perspective views of an assembly of a sampling chamber and a lid handheld compound tester, in accordance with some configurations.
Figure 3B:
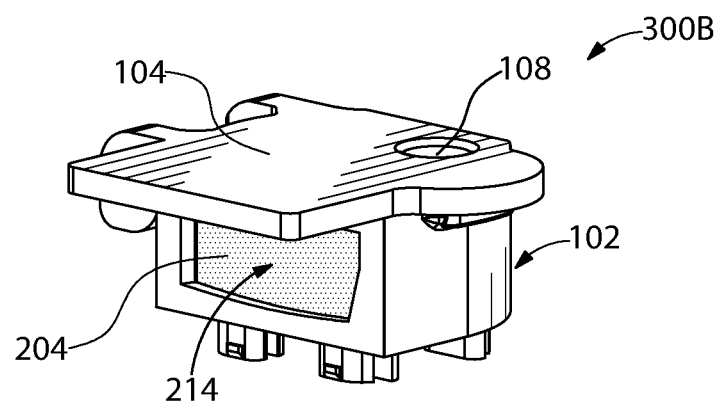

Referring now to FIGS. 3A-3B, perspective views 300A, 300B of an assembly of the sampling chamber 102 and the lid 104 are illustrated, in accordance with some configurations of the present disclosure. In particular, FIG. 3A shows a first view 300A of the assembly of the sampling chamber 102 and the lid 104 with the lid in the open position, and FIG. 3B shows a second view 300B of the assembly of the sampling chamber 102 and the lid 104 with the lid in the closed position. As shown in FIG. 3A, in the open position, the lid 104 is uncoupled from the sampling chamber 102. Further, in the open position, the partition wall 204 may be positioned farther away from the side opening 214 leaving the side opening 214 open with an access to the chute 114 from the sampling chamber 102. As will be understood, the chute 114 may be positioned adjacent to the side opening 214 of the sampling chamber 102.

As shown in FIG. 3B, in the closed position, the lid 104 may be coupled with the sampling chamber 102. Further, in the closed position, the partition wall 204 may extend over the side opening 124 to block the access to the chute 114 from the sampling chamber 102, i.e. block the passage of the liquid or the mixture from the sampling chamber 102 to chute 114. As will be understood, the partition wall 204 may be shaped consistent with the shape of the side opening 124, so as to effectively extend over the side opening 214. For example, as shown in the FIGS. 3A-3B, the partition wall 204 may have a rectangular shape similar to a rectangular shape of the side opening 214.

In some configurations, the partition wall 204 may be molded into the lid 104, and as such made of the same material as the lid 104, i.e. a plastic, a metal, an alloy, etc. However, in some alternate configurations, the partition wall 204 may manufactured separately from the lid 104, and therefore later attached to the lid 104, for example, by gluing, welding, etc.

In some configurations, the lid 104 may include a locking protrusion 304. Further, in such configurations, the sampling chamber 102 may include a lip 306. The locking protrusion 304 may be configured to engage with the lip 306 to lock the lid 104 with the sampling chamber 102 to thereby hold the lid 104 in the closed position.

In some configurations, the lid 104 may include at least one projection 302 projecting perpendicular to the bottom side 104B of the lid 104. The at least one projection 302 may be configured to contact and cut the tablet 202 inside the sampling chamber 102 during the transition of the lid 104 from the open position to the closed position. This is further explained in conjunction with FIGS. 4A-4B.

Figure 4A:
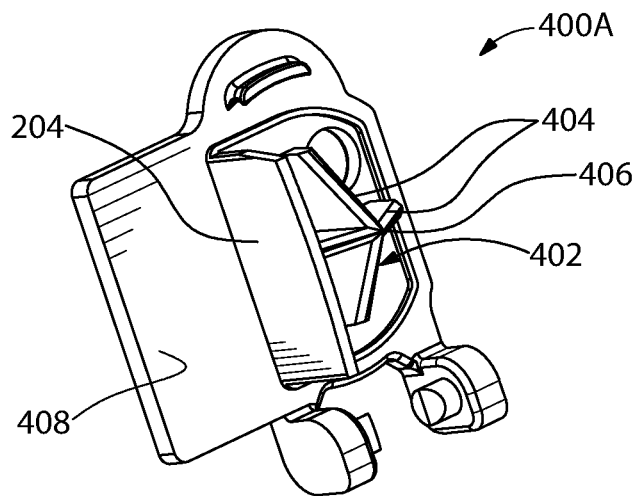
FIGS. 4A-4B illustrate perspective views of lids, in accordance with some configurations.
Figure 4B:
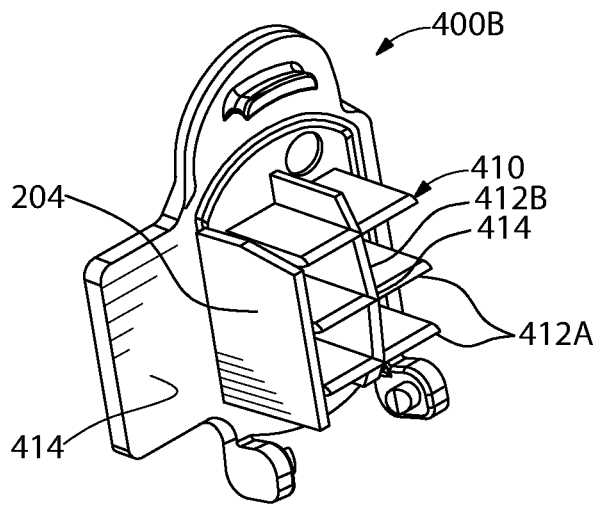

Referring now to FIGS. 4A-4B, perspective views of lids 400A, 400B (corresponding to the lid 104) are illustrated, in accordance with some configurations. In some configurations, as shown in FIG. 4A, the lid 400A may include a projection 402 having a shape resembling a pyramid and projecting perpendicular to a bottom side 408 (corresponding to the bottom side 104B) of the lid 400A. For example, the projection 402 may include two or more walls 404 forming a shape resembling a pyramid, with a middle section of the projection forming a pointed tip 406. The projection 402 may be configured to contact and cut the tablet 202 inside the sampling chamber 102 during the transition of the lid 400A from the open position to the closed position.

In some alternate configurations, as shown in FIG. 4B, the lid 400B may include a projection 410 projecting perpendicular to a bottom side 416 (corresponding to the bottom side 104B) of the lid 400B. For example, the projection 410 may include three walls 412A aligned parallel to each other and a transverse wall 412B aligned perpendicular to the three walls 412A. Further, the projection 410 may include a middle section forming a pointed tip 414. The projection 410 may be configured to contact and cut the tablet 202 inside the sampling chamber 102 during the transition of the lid 400B from the open position to the closed position.

Figure 5:
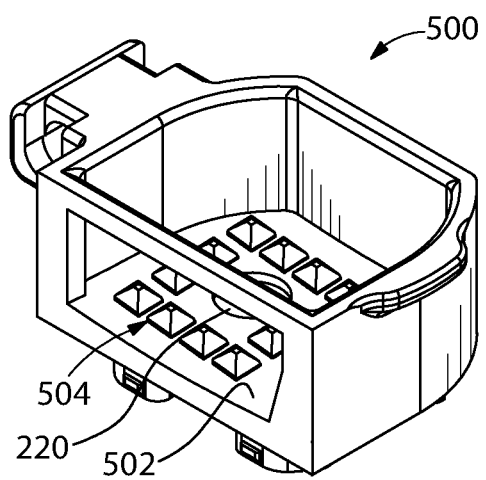
FIG. 5 illustrates a perspective view of a sampling chamber, in accordance with some configurations.

Referring now to FIG. 5, a perspective view of a sampling chamber 500 (corresponding to the sampling chamber 102) is illustrated, in accordance with some configurations of the present disclosure. The sampling chamber 500 may include a bottom surface 502 (corresponding to the bottom surface 218). In some configurations, as shown in FIG. 5, the bottom surface 502 may include a plurality of spikes 504 pointing towards the bottom side of the lid (not shown in FIG. 5) and away from the bottom surface 502 of the sampling chamber 500. During the transition of the lid from the open position to the closed position (i.e. the cut position), the tablet 202 inside the sampling chamber 500 may be sandwiched between the plurality of spikes 504 and the at least one projection (i.e. the projection 402 or the projection 410) of the lid. As will be understood, the combination of the plurality of spikes 504 and the at least one projection may help in effectively crushing the tablet in the cut position. As will be further understood, the effective crushing of the tablet 202 may be necessary to create a proper mixture of the segments of the tablet 202 and the liquid when the liquid is supplied inside the sampling chamber 500.

In some configurations, each spike of the plurality of spikes 504 may be shaped like a pyramid with a pointed tip. Further, in some configurations, the plurality of spikes 504 may be formed within the bottom surface 502 of the sampling chamber 500. In other words, the plurality of spikes 504 may be molded along with the bottom surface 502 during the manufacture of the sampling chamber 500. In alternate configurations, the plurality of spikes 504 may be attached to the bottom surface 502 of the already manufactured sampling chamber 500. To this end, the plurality of spikes 504 may be attached to the bottom surface 502 by way of gluing, welding, etc.

Referring back to FIG. 2, the handheld compound tester 100 may further include the housing 106 which may be adjoining the sampling chamber 102 and maybe fluidically coupled with the sampling chamber 102. The housing 106 may receive the mixture of the liquid and segments of the tablet 202. The mixture may be generated in the sampling chamber 102 upon cutting of the tablet 202 and addition of the liquid inside the sampling chamber 102.

In some configurations, the housing 106 may include a plurality of vertical walls 210 which may define a plurality of compartments 212 inside the housing 106. In some configurations, the plurality of vertical walls 210 may be formed into to the housing 106, for example, via molding. As will be understood, the plurality of vertical walls 210 may be provided for various reasons, including but not limited to, for imparting strength to the structure of the housing 106, ease of manufacturing, etc. Moreover, the plurality of vertical walls 210 provide the required rigidity to the housing 106 (comparable to the rigidity provided by a solid housing) while keeping the housing 106 light weight. One of the plurality of compartments 212, for example, a test compartment 212A may be fluidically coupled with the sampling chamber 102 via the bottom hole 220 to receive the mixture of the liquid and the segment of the tablet 202. In some configurations, the test compartment 212A may be positioned directly below the bottom hole 220 so that the mixture from the sampling chamber 102 passes directly into the test compartment 212A.

In some configurations, the bottom hole 220 may be sized such as to allow at least some of the segments of the table inside the sampling chamber 102 to be passed into the housing 106. This is because liquid may not be able to mix to create a proper mixture during the time period when the liquid is inside the sampling chamber 102. Therefore, by washing along some of the segments from the sampling chamber 102 to the housing 106, some extra time is gained to form the segments to the dissolved in the liquid and create the proper mixture inside the housing 106 instead.

In some configurations, a profile of the test compartment 212A may be identical to, or slightly less than a profile of the test strip 110, so as to allow the test strip 110 to get inserted inside the test compartment 212A. Further, in some configurations, the plurality of compartments 212 may be fluidically coupled with each other. To this end, for example, each of the plurality of vertical walls 210 may include a hole towards a bottom end of the wall that allows the mixture to be evenly distributed in the plurality of compartments 212.

In some configurations, the test strip 110 may be disposed within test compartment 212A of the plurality compartments 212 of the housing 106. Once the mixture is received inside the housing 106 from the sampling chamber 102, the test strip 110 may contact the mixture received in the test compartment 212A. As mentioned above, upon contacting the mixture, the test strip 110 may indicate a presence of the target compound in the mixture. The test strip 110 may be configured to be visible to a user. To this end, in some configurations, the housing 106 may include the cut-out window 112 and the test strip 110 may be positioned adjacent to the cut-out window 112. Alternately the entire housing 106 may be transparent. As such, the test strip 110 positioned inside the housing 106 may be visible to the user through the housing 106.

In some configurations, the handheld compound tester 100 may further include the chute 114 which may be defined adjacent to the sampling chamber 102. The chute 114 may be configured to receive remaining segments of the tablet 202 created upon cutting of the tablet. In other words, while some of the segments created upon cutting of the tablet 202 may be directed into the housing 106 in form of the mixture with the liquid, the remaining segments may pass into the chute 114. These segments in the chute 114 are therefore not exposed to the liquid and can later be recollected by a user. The housing 106 and the chute 114 are further explained in detail in conjunction with FIGS. 6-7.

Figure 6A:
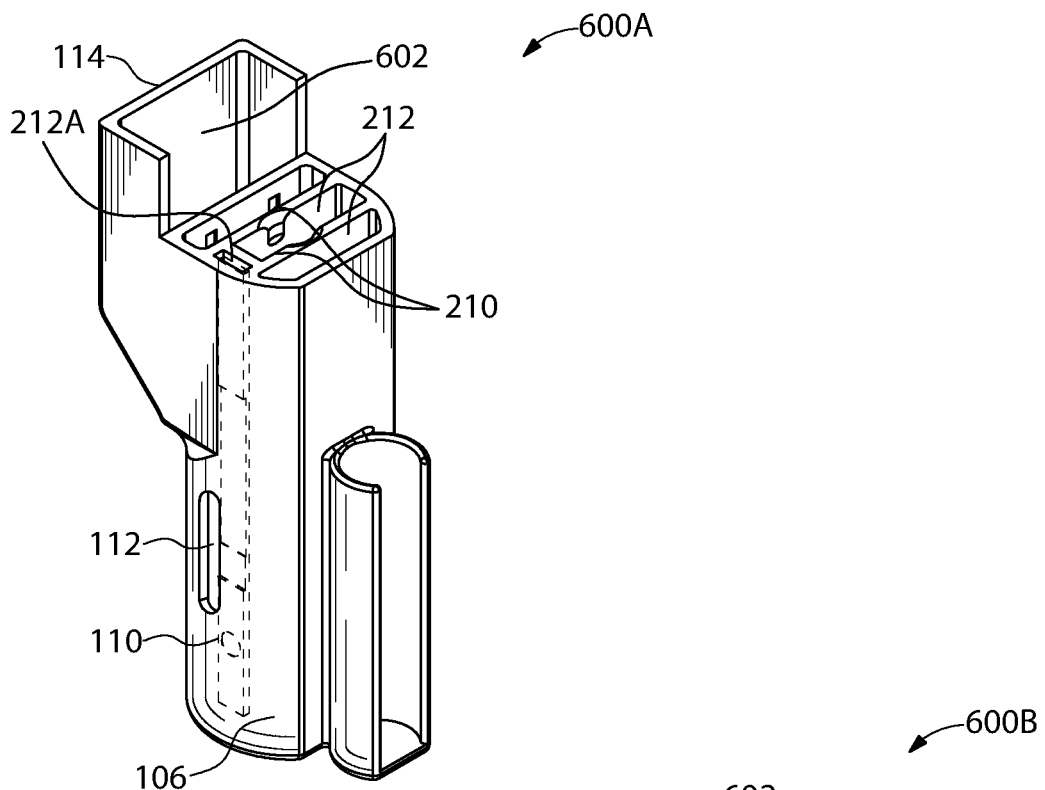
FIGS. 6A-6B illustrate different perspective views of an assembly of a housing and a chute of the handheld compound tester of FIG. 1, in accordance with some configurations.
Figure 6B:
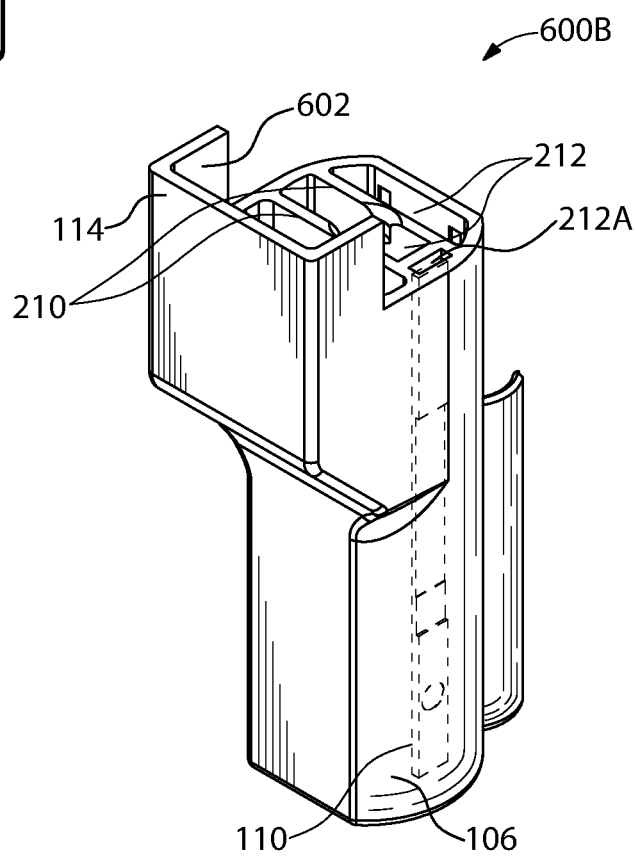

Referring now to FIGS. 6A-6B, different perspective views 600A, 600B of an assembly of the housing 106 and the chute 114 of the handheld compound tester 100 are illustrated, in accordance with some configurations of the present disclosure. As shown in FIG. 6A, the housing 106 may include the plurality of vertical walls 210 defining the plurality of compartments 212 in the housing. Further, the test strip 110 (shown in dotted profile) may be disposed within the test compartment 212A of the housing 106. As will be appreciated, this design of the housing 106 allows for an easy assembly of the test strip 110 with the housing 106 by simply sliding in the test strip 110 inside the test compartment 212A.

For example, in some configurations, as shown in FIG. 6A, the cut-out window 112 may be formed as a cut-out opening in the housing 106. Further, a transparent sheet may be provided over this cut-out opening to fluidically seal the cut-out opening to thereby prevent any leakage of the liquid or the mixture from the housing 106. In alternate configurations, as shown in FIG. 6B, the entire housing 106 may be transparent. As such, the test strip 110 positioned inside the housing 106 may be visible to the user through the housing 106.

Further, as shown in FIGS. 6A-6B, the chute 114 may include an open top face 602, such that segments of the tablet 202 from the chute 114 can be retrieved by the user via the open top face 602.

Referring once again to FIG. 2, the handheld compound tester 100 may further include the liquid ampoule 116. The liquid supplied to the sampling chamber 102 may be retrieved from the liquid ampoule 116 which may be configured to store a predetermined volume of the liquid. The liquid ampoule 116 may be detachably attached to the handheld compound tester 100, in particularly to the housing 106 via the holder 120. The liquid ampoule 116 may include the dispensing head 118 to dispense the liquid inside the liquid ampoule 116. This is further explained in conjunction with FIGS. 7A-7B.

Figure 7A:
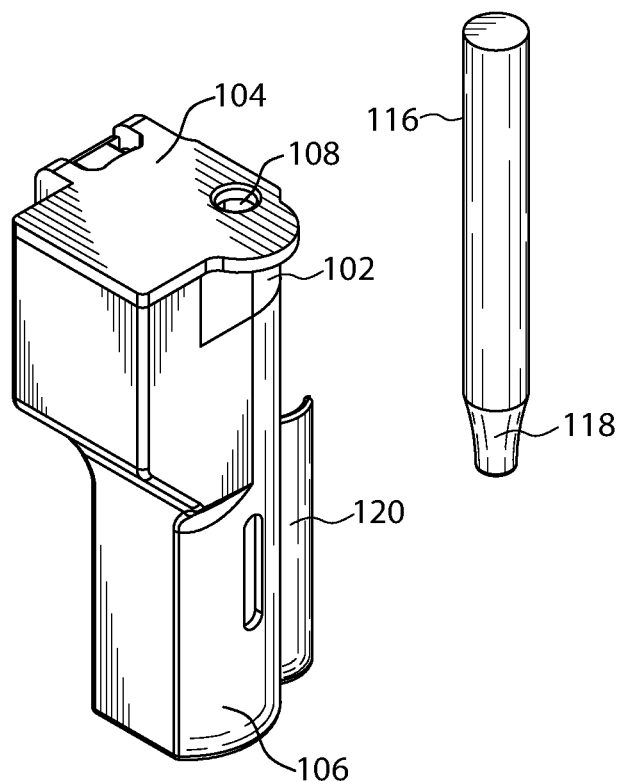
FIGS. 7A-7B illustrate perspectives views of the handheld compound tester including a liquid ampoule, in accordance with some configurations.
Figure 7B:
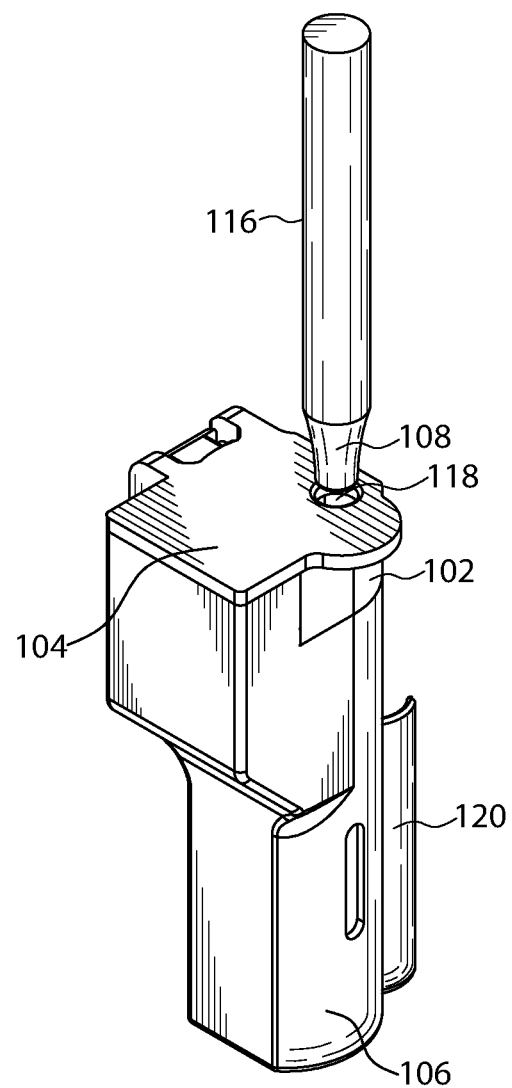

Referring now to FIGS. 7A-7B, perspectives views 700A, 700B of the handheld compound tester 100 including the liquid ampoule 116 are illustrated, in accordance with some configurations of the present disclosure. As shown in FIG. 7A, the liquid ampoule 116 may be configured to be disengaged from the housing 106 of the handheld compound tester 100. The liquid ampoule 116 may include the dispensing head 118. Further, as shown in FIG. 7B, the dispensing head 118 of the liquid ampoule 116 may be configured to fit into the opening 108 of the lid 104 to supply the liquid to the sampling chamber 102. In some configurations, the liquid ampoule 116 may be squeezable, such that, upon being squeezed, the liquid inside the liquid ampoule 116 is pushed out via the dispensing head 118 and supplied to the sampling chamber 102. Alternately, the liquid ampoule 116 may include a piston (not shown in FIGS. 7A-7B) and a cylinder assembly with the piston being configured to be pushed inside to push water from the cylinder into the sampling chamber 102.

Figure 8A:
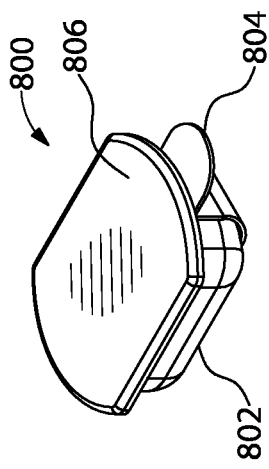
FIGS. 8A-8F illustrate various views of a liquid tub, in accordance with some configurations.
Figure 8B:
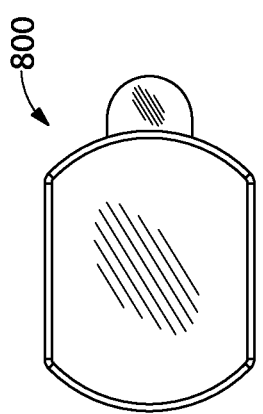
Figure 8C:
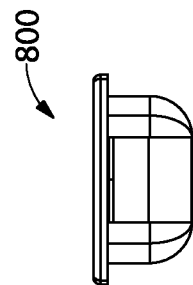
Figure 8E:
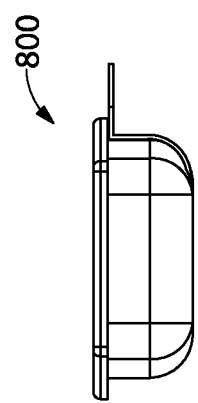
Figure 8D:
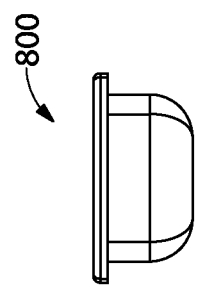
Figure 8F:
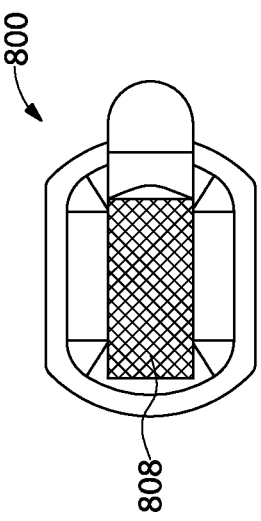

In some configurations, instead of the liquid ampoule 116, the handheld compound tester 100 may include a liquid tub, as shown in FIGS. 8A-8F. Referring now to FIG. 8A, a perspective view of a liquid tub 800 is illustrated in accordance with some configurations. FIGS. 8B-8E illustrate a top view, a front view, a rear view, and a side view, respectively of the liquid tub 800, in accordance some configurations. Further, FIG. 8F illustrates a bottom view of the liquid tub with a pull tab removed, in accordance some configurations.

The liquid tub 800 may be configured to be provided as part of the handheld compound tester 100 (not shown in FIG. 8A), for example, detachably attached to the lid 104. In some configurations, the liquid tub 800 may include a tub body 802, a pull tab 804, and a hard top 806. For example, the tub body 802 may be made of a low density polyethylene (LDPE) sheet.

Further, the hard top 806 may be made of acrylonitrile butadiene styrene (ABS) plastic. By way of an example, a width of the hard top 806 may be 14.80 millimeters (mm), a length of the hard top 806 may be 19.8 mm, and a thickness of the hard top 806 may be 1 mm. Further, a width of the pull tab 804 may be 6 mm, and a length of the pull tab 804 may range between 8 mm and 15 mm. Further, a depth of the tub body 802 may be 6 mm.

In some configurations, similar to the liquid ampoule 116, the liquid tub 800 may be configured to store the predetermined volume of the liquid. In order to supply the liquid from the liquid tub 800 to the sampling chamber 102, the liquid tub 800 may be detached from the lid 104. Thereafter, the pull tab 804 may be removed by tearing away the pull tab 804 from the tub body 802 to expose a vent 808, as shown in FIG. 8F. The liquid may then be supplied to the sampling chamber 102 by aligning this vent 808 with the opening 108 of the lid 104.

Figure 9A:
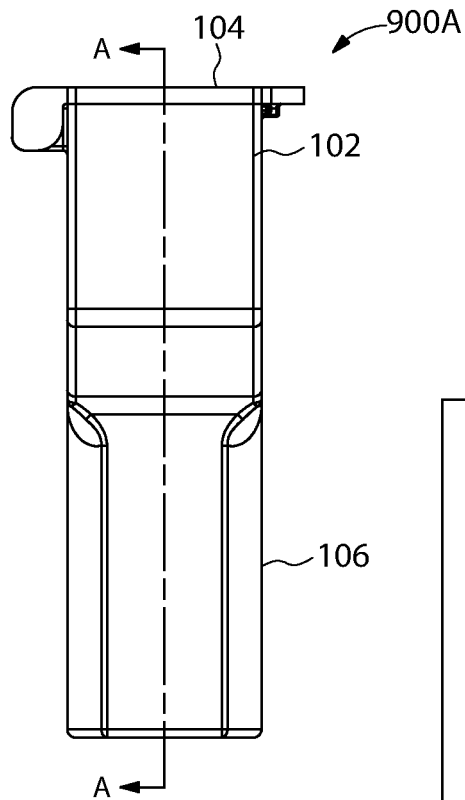
FIG. 9A illustrates a side view of the handheld compound tester of FIG. 1, in accordance with some configurations.
Figure 9B:
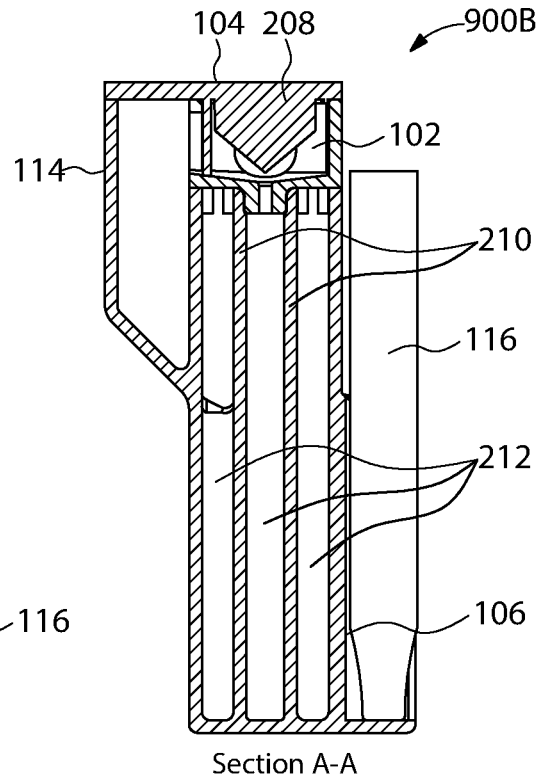
FIG. 9B illustrates a first sectional view of the handheld compound tester of FIG. 9A along a section line A-A' in a first configuration, in accordance with some configurations.
Figure 9C:
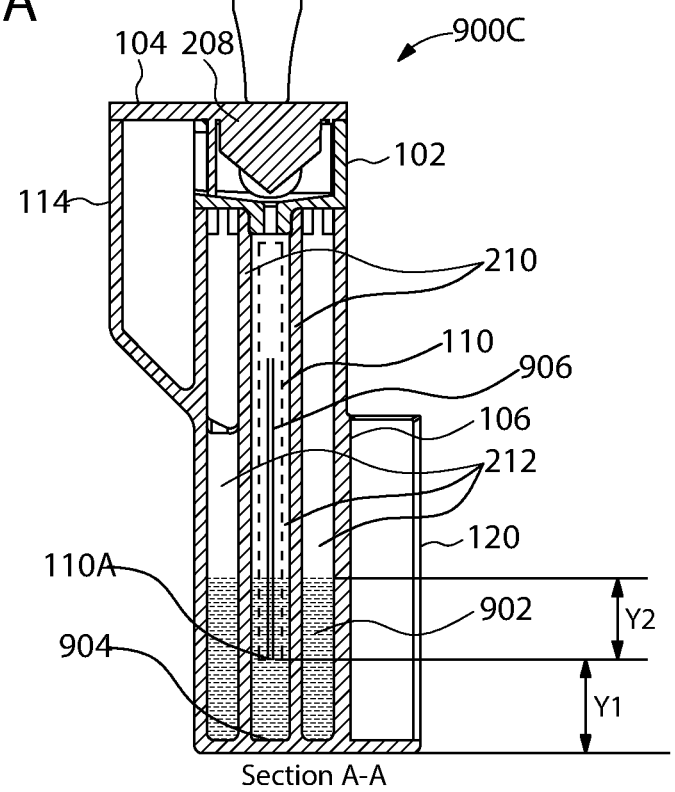
FIG. 9C illustrates a second sectional view of the handheld compound tester of FIG. 9A along the section line A-A' in a second configuration, in accordance with some configurations.

Referring now to FIGS. 9A-9C, different views of the handheld compound tester 100 are illustrated, in accordance with some configurations of the present disclosure. FIG. 9A illustrates a side view 900A of the handheld compound tester 100. FIG. 9B illustrates a first sectional view 900B of the handheld compound tester 100 of FIG. 9A along a section line A-A' in a first configuration. FIG. 9C illustrates a sectional view 900C of the handheld compound tester 100 of FIG. 9A along the section line A-A' in a second configuration. It should be noted that the first configuration of the handheld compound tester 100 may correspond to the housing 106 being empty of the mixture, and the second configuration of the handheld compound tester 100 may correspond to the housing 106 having received the mixture from the sampling chamber 102.

As shown in FIG. 9B, in the first configuration, the housing 106 of the handheld compound tester 100 may not include any mixture of the liquid and the segments of the tablet 202. As such, the plurality of compartments 212 defined inside the housing 106 may be empty, i.e. without any mixture. As will be understood, the test strip 110 (not shown in FIGS. 9A-9C) may not provide any indication about the presence of the compound within the mixture.

Further, as shown in FIG. 9C, in the second configuration, the housing 106 of the handheld compound tester 100 may include the mixture 902 of the liquid and the segments of the tablet 202. In other words, in the second configuration, the housing 106 may have received the mixture 902 from the sampling chamber 102. As such, the plurality of compartments 212 defined inside the housing 106 may include the mixture 902. Further, the mixture 902 in the test compartment may contact the test strip 110 from below. As will be appreciated by those skilled in the art, owing to the capillary action, the mixture 902 (in the liquid state) may move along the length of the test strip 110. Further, the mixture 902, depending upon the presence of the target compound in the mixture 902, may cause the test strip 110 to provide an indication 906 of the presence of the compound in the mixture 902. It should be noted that, the test strip 110 (not shown in FIGS. 9A-9C) may not provide the indication 906 for a specific period of time, for example, one or two minutes. This is because the chemical reaction (which is responsible for generating that indication on the test strip) of the compound with the test strip may take that specific period of time to complete. In some configurations, the indication 906 may include appearance of two straight lines along the length of the test strip 110. In other words, an appearance of two straight lines along the length of the test strip 110 indicates that the mixture 902 contains the target compound. Alternatively, in some configurations one straight line along the length of the test strip 110 indicates that the mixture 902 contains the target compound.

In some configurations, the test strip 110 may be positioned in a way that the test strip 110 is elevated by a predetermined distance (y1) from a bottom surface 904 the housing 106. For example, as shown in FIG. 9C, a bottom end 110A of the test strip 110 may be elevated by 1-2 millimeters (i.e. y=1-2 millimeters) from the bottom surface 904 of the housing 106.

In some configurations, the test compartment 212A of the housing 106 may be configured to receive a predefined maximum volume of the liquid mixture 902 which may contact a maximum predefined length (y2) of the test strip 110 from the bottom end 110A of the test strip 110. This is because the test strip 110 may be able to provide an accurate indication of the presence of the compound in the mixture when it is in contact with that predefined maximum amount of mixture 902. A larger amount of liquid mixture 902 coming in contact with the test strip 110 may cause inaccurate indications. To this end, the housing 106 may be configured to evenly distribute the liquid mixture 902 entering in the housing 106 among the plurality of compartments 212 including the test compartment 212A. As shown in FIG. 9C, the mixture (shown in solid profile in FIG. 9C) may be evenly distributed in the plurality of compartments 212 including the test compartment 212A. This even distribution of the mixture 902 in the plurality of compartments 212 may be provisioned by the hole (not shown in FIG. 9) towards the bottom end of the plurality of vertical walls 210 that fluidically couples the plurality of compartments 212 with each other.

Figure 10:
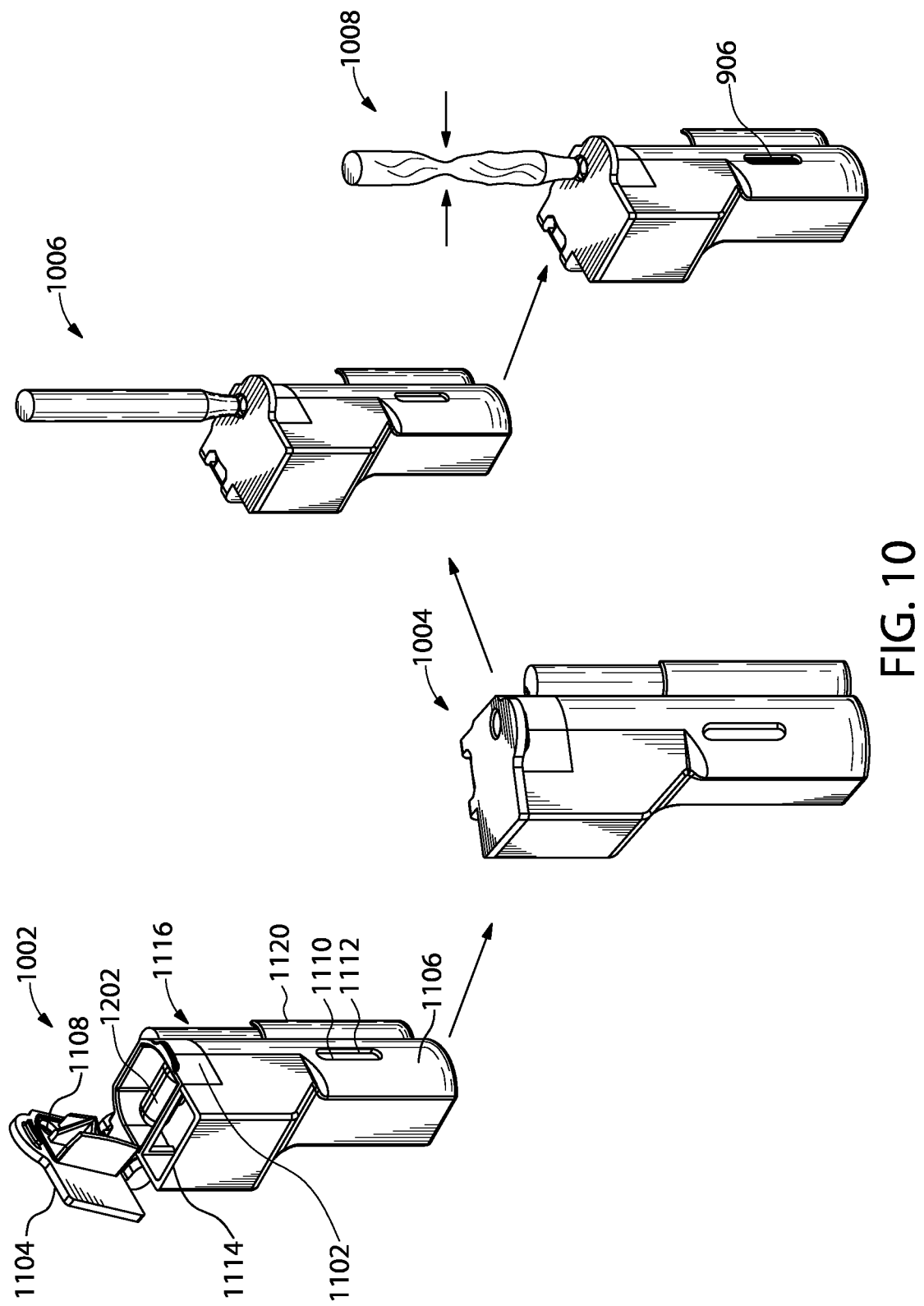
FIG. 10 is a process flow diagram of a process of processing and detecting presence of a target compound in a tablet, in accordance with some configurations.

Referring now to FIG. 10, a process flow diagram of a process 1000 of processing and detecting presence of the target compound in the tablet 202 is illustrated, in accordance with some configurations of the present disclosure. At step 1002, the handheld compound tester 1002 for processing and detecting the presence of the compound in the tablet 1202 may be provided. As explained above with reference to FIGS. 1-9, the handheld compound tester 1002 may include the sampling chamber 1102. The sampling chamber 1102 may include the at least one inner boundary wall 1216, and the bottom surface 1218 which may include the bottom hole 1220. The handheld compound tester 1002 may further include the lid 1104 which may be couplable with the sampling chamber 1102 via the hinged coupling. The lid 1104 may include the top side 1104A and the bottom side 1104B. The lid 1104 may further include the opening 1108 to provide a supply of the liquid into the sampling chamber 1102. The lid 1104 may be configured to transition between the open position and the closed position. In the open position, the lid 1104 is uncoupled from the sampling chamber 1102. In the closed position, the lid 1104 is coupled with the sampling chamber 1102 to thereby define an inner space along with the at least one inner boundary wall 1216 and the bottom surface 1218. The handheld compound tester 1002 may further include housing 1106 defined vertically below the sampling chamber 1102. The housing may be fluidically coupled with the sampling chamber 1102 via the bottom hole 1220. The test strip 1110 may be disposed within the housing 1106.

Further, in some configurations, the handheld compound tester 100 may include the chute 1114 defined adjacent to the sampling chamber 1102. The chute 1114 may be configured to receive some segments of the tablet 1202 created upon cutting of the tablet 1202 during the transition of the lid 1104 from the open position to the closed position. In some configurations, the at least one inner boundary wall 1215 may include side opening 1214, such that the chute 1114 may receive the remaining segments of the tablet 1202 via the side opening 1214. In some configurations, the lid 1104 may include the partition wall 1204 projecting substantially perpendicular to the bottom side 1104B of the lid 1104. In some configurations, the lid 1104 may further include at least one projection 208 projecting perpendicular to the bottom side 1104B of the lid 1104. The at least one projection 1208 may be configured to contact and cut the tablet 1202 inside the sampling chamber 1102 during the transition of the lid 1104 from the open position to the closed position. In some configurations, the bottom surface 1218 of the sampling chamber 1102 may include the plurality of spikes 1504 pointing towards the bottom side 104B of the lid 1104.

In some configurations, the handheld compound tester 1002 may include the liquid ampoule 1116 which may store a predetermined volume of liquid. The liquid ampoule 1116 may be configured to be detachably attached to the housing 1106. The liquid ampoule 1116 may include the dispensing head 1118 to dispense the liquid stored inside the liquid ampoule 1116, such that the dispensing head 1118 is configured to fit into the opening 1108 of the lid 1104.

Further, at step 1002, in the open position, the lid 1104 may be uncoupled from the sampling chamber 1102. Furthermore, at step 1002, the tablet 1202 may be positioned inside the sampling chamber 1102 with the lid 1104 in the open position. It should be noted that at the step 1002, the liquid ampoule 1116 may be attached to the housing 1106, i.e. intact within the holder 1120. Once the tablet 202 is positioned inside the sampling chamber 1102, the lid 1104 may be transitioned from the open position to the closed position.

In some configurations, the housing 1106 may include the plurality of vertical walls 1210 defining a plurality of compartments 1212 including the test compartment 1212A. The test compartment 1212A may be fluidically coupled with the sampling chamber 1102 via the bottom hole 1220 and configured to receive the mixture 1902 of the liquid and the segment of the tablet 1202 from the sampling chamber 1102. Further, the test compartment 1212A may be configured to receive a maximum predefined volume of the mixture. The test strip 1110 may be disposed within the test compartment 1212A. Further, the maximum predefined volume of the mixture may contact a maximum predefined length of the test strip 1110 from a bottom end of the test strip.

At step 1004, the lid 1104 may be transitioned in the closed position, i.e., the transitioned of the lid 1104 from the open position to the closed position may be complete. The transition may take place by rotating the lid 1104 about the hinged coupling, i.e. the first hinge member 1206A of the lid 1104 and the second hinge member 1206B of the sampling chamber 1102. Additionally, upon transitioning of the lid 1104 into the closed position, the locking protrusion 304 of the lid may be engaged with the lip 306 of the sampling chamber 102 to lock the lid 104 with the sampling chamber 102. The lid 104 may be coupled with the sampling chamber 102 to thereby define an inner space along with the at least one inner boundary wall 216 and the bottom surface 218. Further, at the step 1004, the liquid ampoule 116 may still be attached to the housing 106, i.e. intact within the holder 120.

It should be noted that during the transition from the open to the closed position, the lid 104 may cut the tablet 202 inside the sampling chamber 102. The tablet 202 may be cut to generate a plurality of segments of the tablet. As will be understood, the cutting of the tablet 202 may be occur by way of the tablet 202 being sandwiched between the at least one projection 208 and the plurality of spikes 504. Further, during the transition of the lid 104 from the open position to the closed position, the partition wall 204 projecting substantially perpendicular to the bottom side 104B of the lid 104 may cause some segments of the tablet to be moved into the chute 114 while some segments are retained within the sampling chamber. Furthermore, in the closed position of the lid 104, the partition wall 204 may extend over the side opening 214 to shut the side opening 214. As a result, the side opening 214 may block passage of the liquid or the mixture 902 from the sampling chamber 102 to chute 114 when the liquid is added to the sampling chamber 102 in the subsequent step.

At step 1006, once the lid 104 has transitioned into the closed position, the liquid ampoule 116 may be detached from the holder 120 and further fitted to the opening 108 of the lid 104. In particular, the dispensing head 118 of the lid 104 may be fit into the opening 108 of the lid 104 to dispense the liquid stored inside the liquid ampoule 116. In some configurations, the dispensing head 118 may have a circular profile similar to a circular profile of the opening 108 to therefore allow the dispensing head 118 to fit in the opening 108. Further, in some configurations, the dispensing head 118 may be made from a flexible material, for example a plastic, or a rubber, etc. which may further aid in the fitting of the dispensing head 118 in the opening 108.

At step 1008, the liquid may be supplied from liquid ampoule 116 to the sampling chamber 102 to create the mixture 902 of the liquid and segments of the tablet 202 already present inside the sampling chamber 102. In some configurations, the liquid ampoule 116 may be squeezable. Therefore, in order to supply the liquid from the liquid ampoule 116 to the sampling chamber 102, the liquid ampoule 116 may be squeezed, as shown in FIG. 10. For example, the liquid ampoule 116 may be squeezed manually by pressing the liquid ampoule 116 between an index finger and a thumb of the user. Upon being squeezed, the liquid ampoule 116 may be configured to supply the liquid stored inside the liquid ampoule 116 to the sampling chamber 102 via the dispensing head 118. Once the liquid is received inside the sampling chamber 102, the mixture 902 of the liquid and the segments of the tablet 202 already present inside the sampling chamber 102 may be created.

The mixture 902 may then pass to the test compartment 212A of the housing 106 via the bottom hole 220 of the sampling chamber 102. The test compartment 212A may be configured to receive a maximum predefined volume of the mixture 902. As the test strip 110 is disposed within the test compartment 212A, the maximum predefined volume of the mixture may contact a maximum predefined length of the test strip 110 from a bottom end of the test strip 110. Upon contacting, the test strip 110 may indicate a presence of the target compound within the mixture 902.

As such, further at step 1008, the test strip 110 may be viewed by the user. To this end, in some configurations, the housing 106 may include the cut-out window 112 located along the test compartment 212A and the test strip 110 may be positioned adjacent to the cut-out window 112, such that at least a portion of the test strip 110 is visible to the user via the cut-out window 112. Alternately, the entire housing 106 may be transparent, to thereby allow at least a portion of the test strip 110 to be visible to the user through the transparent housing 106.

Additionally, the unused segments of the tablet 202 that are moved into the chute 114 may be retrieved by the user. To this end, in some configurations, the chute 114 may include the open top face 602, such that segments of the tablet 202 from the chute 114 can be retrieved by the user via the open top face 602. It should be noted that the lid 104 may be configured to cover the open top face 602, in the closed position of the lid. Therefore, in order to retrieve the segments of the tablet 202 from the chute 114, first the lid 104 may be flipped for allowing access to the chute 114 via the open top face 602.

As will be understood, if the test strip 110 indicates a positive presence of the compound (e.g. fentanyl) inside the mixture 902 (i.e. inside the tablet 202), the tablet 202 may be considered unsafe. As such, upon retrieving the unused segments from the chute 114, the unused segments of the tablet may be discarded or reported to a drug authority. However, if the test strip 110 indicates a negative presence of the target compound inside the mixture and the tablet 202 (i.e. the target compound is absent), the tablet 202 may be considered as safe, and therefore deemed fit for consumption. Since only a small percentage of segments of the tablet 202 are left inside the sampling chamber 102 for detecting the compound and majority of the tablet segments are moved to the chute 114, therefore, majority of the tablet can be retrieved and can be consumed by the user.

Figure 11A:
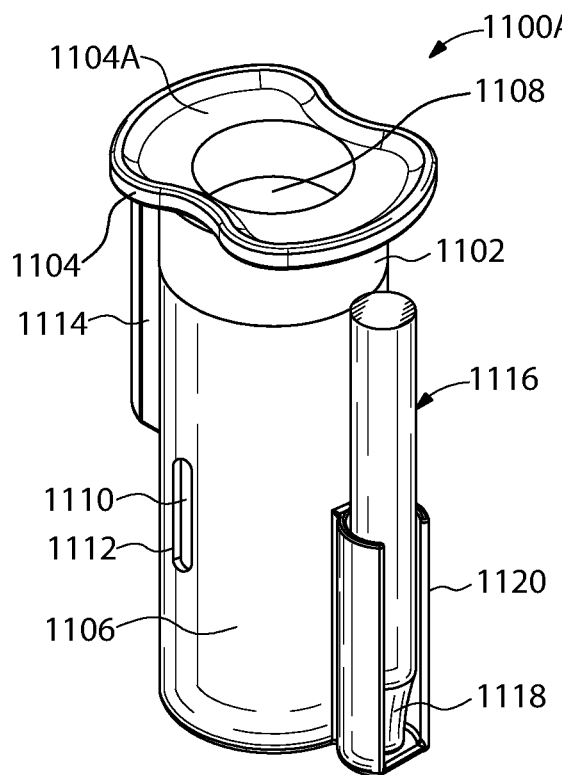
FIGS. 11A-11B illustrates perspective views of an exemplary handheld compound tester to process and detect presence of a target compound in a tablet, in a closed position of a lid, in accordance with another configuration of the present disclosure.
Figure 11B:
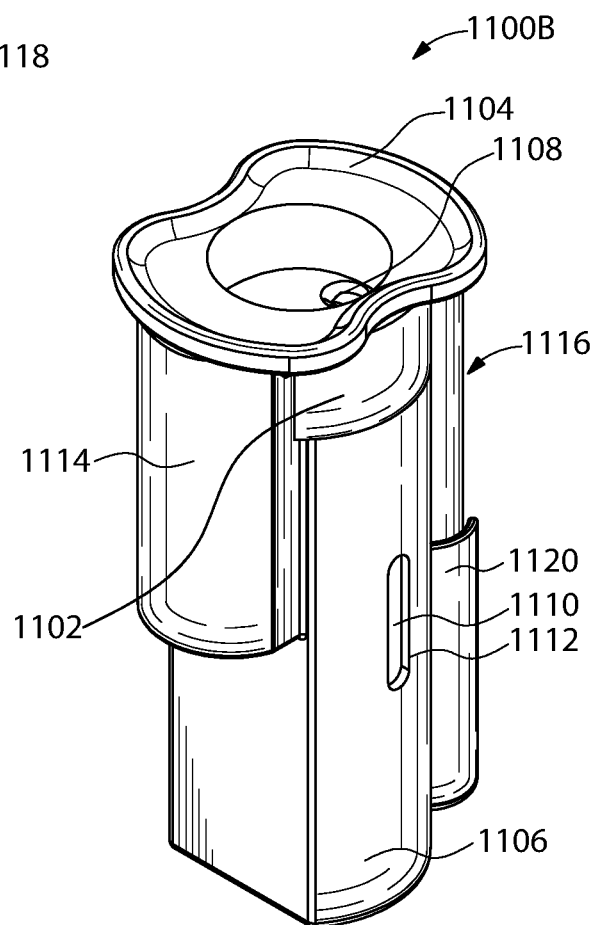

Referring now to FIGS. 11A-11B, perspective views 1100A and 1100B of an exemplary handheld compound tester 1100 to process and detect presence of a target compound in a tablet, in a closed position of a lid, are illustrated in accordance with some configurations of the present disclosure. The handheld compound tester 1100 may include a sampling chamber 1102 configured to receive the tablet (not shown in FIGS. 11A-11B) that is to be tested. As mentioned earlier, the term tablet may refer to any pharmaceutical or recreational drug in any configuration including, but not limited to, a solid, a paste, or a liquid, and having any shape and size including a spherical, a disc-like, or an oval shape. The handheld compound tester 1100 may further include a lid 1104 couplable with the sampling chamber 1102. The lid 1104 may include an opening 1108 to provide a supply of liquid to the sampling chamber 1102. Further, the lid 1104 may include a top side 1104A and a bottom side (not shown in FIG. 11).

As shown in the FIGS. 11A-11B, in the closed position of the lid 1104, the lid 1104 may be coupled with the sampling chamber 1102 to define an inner space which may receive the tablet. The lid 1104 may be configurable between an open position and the closed position. In the open position, the lid 1104 may be uncoupled from the sampling chamber 1102 (as later shown in FIG. 20) As further shown in FIGS. 11A-11B, in the closed position, the lid 1104 may be uncoupled from the sampling chamber 1102. The lid 1104 may be further configurable in a cut position which may be different than the open position and the closed position. In the cut position, the lid 1104 may be configured to cut the tablet inside the sampling chamber 1102. In particular, during the transition from the open position to the closed position, the lid 1104 may cut the tablet into multiple segments inside the sampling chamber 1102. Thereafter a liquid, for example water, may be supplied to the sampling chamber 1102 that may create a mixture with some of the segments of the tablet.

The handheld compound tester 1100 may further include a housing 1106 which may adjoin the sampling chamber 1102 and may be fluidically coupled with the sampling chamber 1102. The housing 1106 may be configured to receive the mixture of the liquid and the segments of the tablet.

In some configurations, a test strip 1110 may be disposed within the housing 1106. The test strip 1110 may be configured to contact the mixture received in the housing 1106, and upon contacting, further configured to indicate a presence of the target compound in the mixture and therefore in the tablet. For example, upon contacting the mixture containing the target compound, for example, fentanyl, a chemical reaction of the target compound with the test strip (for example, with a chemical provided on the test strip) may take place which may cause a color change of a section of the test strip 1110. However, if the mixture does not contain the target compound, no such chemical reaction or the color change of the test strip 1110 may take place. An occurrence of such color change may therefore indicate presence of the target compound in the mixture and the tablet. The test strip 1110 may be configured to be visible to a user. To this end, for example, the housing 1106 may include a cut-out window 1112 with the test strip 1110 being positioned adjacent to the cut-out window 1112. Alternately, the housing 1106 itself may be transparent to allow the test strip 1110 to be visible to the user. In some configurations, presence of the target compound may cause no visible change to the test strip 1110 or a simple control mark that may appear.

In some configurations, the handheld compound tester 1100 may further include a chute 1114 adjoining the sampling chamber 1102. The chute 1114 may be configured to receive remaining segments of the tablet created upon cutting of the tablet. While some of the segments created upon cutting of the tablet may be directed into the housing 1106 in form of the mixture with the liquid, the remaining segments may be passed into the chute 1114. The segments of the tablet in the chute 1114 are therefore not exposed to the liquid and can later be recollected by the user.

The liquid to be supplied into the sampling chamber 1102 may be retrieved from a liquid ampoule 1116. Similar to the liquid ampoule 116, the liquid ampoule 1116 may be configured to store a predetermined volume of liquid and may be provided as detachably attached to the handheld compound tester 1100, in particularly to the housing 1106 via a holder 1120. In some configurations, the holder 1120 may be formed into the housing 1106 or separately attached to the housing 1106.

The liquid ampoule 1116 may include a dispensing head 1118 to dispense the liquid which is stored inside the liquid ampoule 1116. The dispensing head 1118 may be configured to fit into the opening 1108 of the lid 1104 to supply the liquid to the sampling chamber 1102. In some configurations, the liquid ampoule 1116 may be squeezable, such that, upon being squeezed, the liquid inside the liquid ampoule 1116 is pushed out via the dispensing head 1118 and supplied to the sampling chamber 1102. In some alternate configurations, the liquid ampoule 1116 may include a piston-cylinder assembly, such that the liquid inside the cylinder may be pushed out by pushing the piston and therefore supplied to the sampling chamber 1102.

Figure 12:
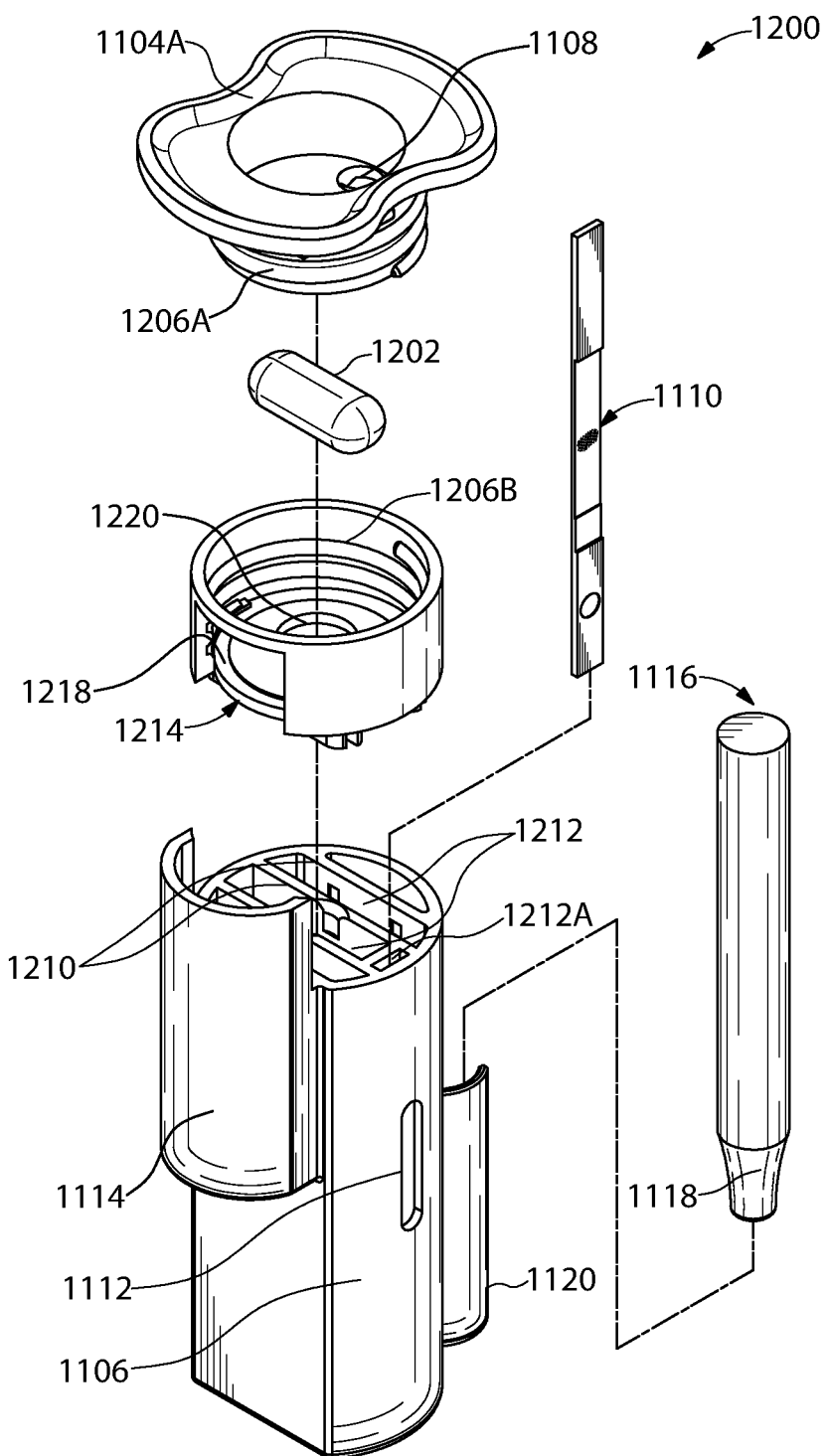
FIG. 12 illustrates an exploded view of the handheld compound tester of FIGS. 11A-11B, in accordance with some configurations.

Referring now to FIG. 12, an exploded view 1200 of the handheld compound tester 1100 of FIGS. 11A-11B is illustrated, in accordance with some configurations of the present disclosure. As already mentioned above, the handheld compound tester 1100 may include the sampling chamber 1102, the lid 1104, the housing 1106, the test strip 1110, the chute 1114, and the liquid ampoule 1116.

The sampling chamber 1102 may be configured to receive a tablet 1202 that is to be tested. The sampling chamber 1102 may include at least one inner boundary wall 1216. For example, as shown in FIG. 12, the sampling chamber 1102 may have a substantially circular profile and therefore may include a single inner boundary wall 1216. The sampling chamber 1102 may further include a bottom surface 1218 which may further include a bottom hole 1220. The sampling chamber 1102 may be made of any rigid material selected from a plastic, a metal, an alloy, etc.

The lid 1104 may include the top side 1104A and a bottom side 1104B. Further, the lid 1104 may include the opening 1108 across the top side 1104A and bottom side 1104B (not visible in FIG. 12). This opening 1108 may be used to provide a supply of liquid to the sampling chamber 1102.

The lid 1104 may be couplable with the sampling chamber 1102. In some configurations (as shown in FIGS. 11-20), the lid 1104 may be couplable with the sampling chamber 1102 via a thread coupling. To this end, the bottom side 1104B of the lid 1104 may include a threaded head 1206A configured to engage with a threaded portion 1206B of the sampling chamber 1102 to couple the lid 1104 with the sampling chamber 1102 in the closed position. The threaded portion 1206B of the sampling chamber 1102 may be defined along the inner boundary wall 1216 of the sampling chamber 1102. The lid 1104 may therefore by coupled to the sampling chamber 1102 by rotatably tightening the lid 1104 with the threaded portion 1206B of the sampling chamber 1102. The lid 1104 may be made of any rigid material selected from a plastic, a metal an alloy, etc.

In some configurations, the inner boundary wall 1216 of the sampling chamber 1102 may include a side opening 1214. As mentioned above, as the lid 1104 transitions into the cut position, i.e. transitions from the open position to the closed position, the tablet 1202 inside the sampling chamber 1102 is cut into a plurality of segments. While some of the segments may be directed into the housing 1106 in form of the mixture (along with the liquid), some of the segments may be received by the chute 1114 from the sampling chamber 1102 via the side opening 1214. Further, the threaded head 1206A of the lid 1104 may be configured to extend over the side opening 1214 to block passage of the liquid or the mixture from the sampling chamber 1102 to chute 1114. As the lid 1104 transitions from the open position to the closed position, the threaded head 1206A may extend over the side opening 1214. As such, during this transition, some segments of tablet are passed to chute 1114 and some segments are directed into the housing 1106 upon being mixed with the liquid. This is further explained in conjunction with FIGS. 3A-3B.

Figure 13A:
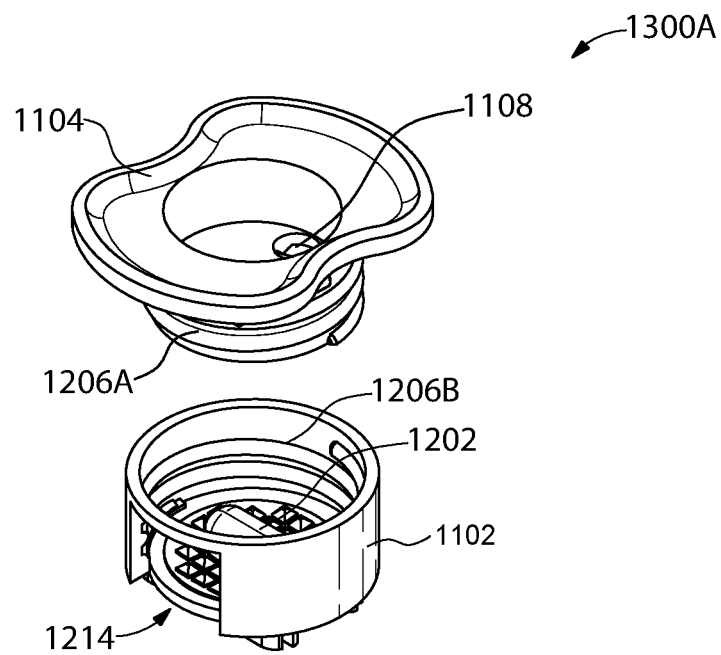
FIGS. 13A-13B illustrate perspective views of an assembly of a sampling chamber and a lid of the handheld compound tester, in accordance with some configurations.
Figure 13B:
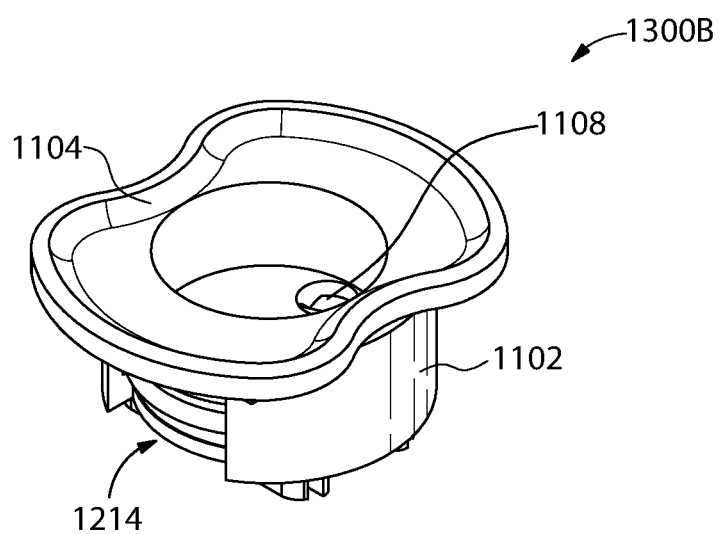

Referring now to FIGS. 13A-13B, perspective views 1300A, 1300B of an assembly of the sampling chamber 1102 and the lid 1104 are illustrated, in accordance with some configurations of the present disclosure. In particular, FIG. 13A shows a first view 1300A of the assembly of the sampling chamber 1102 and the lid 1104 with the lid in the open position, and FIG. 13B shows a second view 1300B of the assembly of the sampling chamber 1102 and the lid 1104 with the lid in the closed position. As shown in FIG. 13A, in the open position, the lid 1104 is uncoupled from the sampling chamber 1102. Further, in the open position, the threaded head 1206A may be away from the side opening 1214 leaving the side opening 1214 open with an access to the chute 1114 from the sampling chamber 1102. As will be understood, the chute 1114 may be positioned adjacent to the side opening 1214 of the sampling chamber 1102.

As shown in FIG. 13B, in the closed position, the lid 1104 may be coupled with the sampling chamber 1102. Further, in the closed position, the threaded head 1206A may extend over the side opening 1214 to block the access to the chute 1114 from the sampling chamber 1102, i.e. block the passage of the liquid or the mixture from the sampling chamber 1102 to chute 1114. As will be understood, the threaded head 1206A may have a shape profile similar to the profile of the side opening 1214, so as to effectively extend over the side opening 1214. For example, as shown in the FIGS. 13A-13B, the threaded head 1206A may have a circular profile similar to the circular profile of the side opening 1214. In some configurations, the threaded head 1206A may be molded into the lid 1104, and as such made of the same material as the lid 1104, i.e. a plastic, a metal, an alloy, etc.

Figure 14:
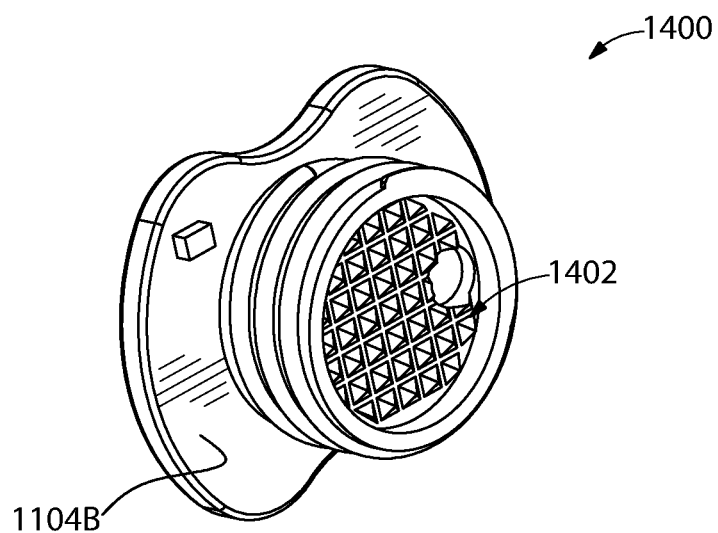
FIG. 14 illustrate a perspective view of a lids of the handheld compound tester, in accordance with some configurations.

Referring now to FIG. 14, a perspective view 1400 of the lid 1104 is illustrated, in accordance with some configurations. In some configurations, as shown in FIG. 14, the bottom side 1104B of the lid 1104 may include a plurality of projections 1402. The plurality of projections 1402 may be configured to contact and cut the tablet 1202 inside the sampling chamber 1102 during the transition of the lid 1104 from the open position to the closed position.

In some configurations, each projection of the plurality of projections 1402 may be shaped like a pyramid with a pointed tip. Further, in some configurations, the plurality of projections 1402 may be formed within the bottom side 1104B of the 1104. In other words, the plurality of projections 1402 may be molded along with the bottom side 1104B during the manufacture of the lid 1104. Alternatively, the plurality of projections 1402 may be attached to the bottom side 1104B of the already manufactured lid 1104 by way of gluing, welding, etc.

Figure 15:
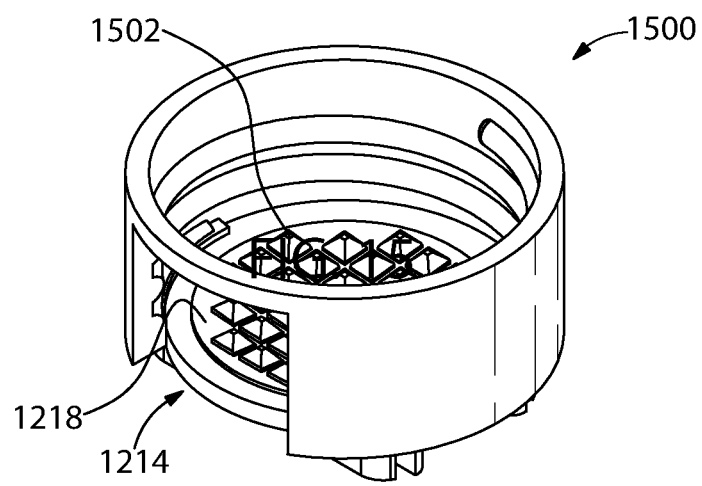
FIG. 15 illustrates a perspective view of a sampling chamber of the handheld compound tester, in accordance with some configurations.

Referring now to FIG. 15, a perspective view 1500 of the sampling chamber 1102 is illustrated, in accordance with some configurations of the present disclosure. The sampling chamber 1102 may include the bottom surface 1218. In some configurations, as shown in FIG. 15, the bottom surface 1218 may include a plurality of spikes 1502 pointing towards the bottom side of the lid (not shown in FIG. 15) and away from the bottom surface 1218 of the sampling chamber 1102. During the transition of the lid 1104 from the open position to the closed position (i.e. the cut position), the tablet 1202 inside the sampling chamber 1102 may be sandwiched between the plurality of spikes 1502 and the plurality of projections 1402 of the lid 1104 that may help in effectively crushing the tablet 1202.

In some configurations, each spike of the plurality of spikes 1502 may be shaped like a pyramid with a pointed tip. Further, in some configurations, the plurality of spikes 1502 may be formed within the bottom surface 1218 of the sampling chamber 1102. In other words, the plurality of spikes 1502 may be molded along with the bottom surface 1218 during the manufacture of the sampling chamber 1102, or may be attached to the bottom surface 1218 of the already manufactured sampling chamber 1102 by way of gluing, welding, etc.

Referring once again to FIG. 12, the handheld compound tester 1100 may further include the housing 1106 which may be adjoining the sampling chamber 1102 and maybe fluidically coupled with the sampling chamber 1102. The housing 1106 may receive the mixture of the liquid and segments of the tablet 1202. The mixture may be generated in the sampling chamber 1102 upon cutting of the tablet 1202 and addition of the liquid inside the sampling chamber 1102.

In some configurations, the housing 1106 may include a plurality of vertical walls 1210 which may define a plurality of compartments 1212 inside the housing 1106. In some configurations, the plurality of vertical walls 1210 may be formed within the housing 1106, for example, via molding. One of the plurality of compartments 1212, for example, a test compartment 1212A may be fluidically coupled with the sampling chamber 1102 via the bottom hole 1220 to receive the mixture of the liquid and the segment of the tablet 1202. In some configurations, the test compartment 1212A may be positioned directly below the bottom hole 1220 so that the mixture from the sampling chamber 1102 passes directly into the test compartment 1212A. Further, in some configurations, the plurality of compartments 1212 may be fluidically coupled with each other. To this end, for example, each of the plurality of vertical walls 1210 may include a hole towards a bottom end of the wall that allows the mixture to be evenly distributed in the plurality of compartments 1212.

In some configurations, the test strip 1110 may be disposed within test compartment 1212A of the plurality of compartments 1212 of the housing 1106. Once the mixture is received inside the housing 1106 from the sampling chamber 1102, the test strip 1110 may contact the mixture received in the test compartment 1212A, and upon contacting the mixture, the test strip 1110 may indicate a presence of the target compound in the mixture. The test strip 1110 may be configured to be visible to a user. To this end, in some configurations, the housing 1106 may include the cut-out window 1112 and the test strip 1110 may be positioned adjacent to the cut-out window 1112, or the entire housing 1106 may be transparent.

In some configurations, the handheld compound tester 1100 may further include the chute 1114 which may be defined adjacent to the sampling chamber 1102. The chute 1114 may be configured to receive remaining segments of the tablet 1202 created upon cutting of the tablet. While some of the segments created upon cutting of the tablet 1202 may be directed into the housing 1106 in form of the mixture, the remaining segments may pass into the chute 1114. These segments in the chute 1114 are therefore not exposed to the liquid and can later be recollected by a user. The housing 1106 and the chute 1114 are further explained in detail in conjunction with FIGS. 16-17.

Figure 16:
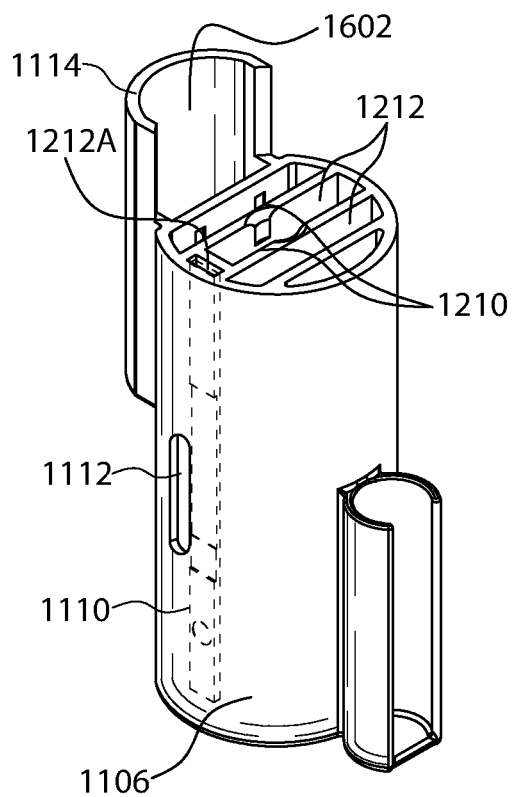
FIGS. 16-17 illustrate different perspective views of an assembly of a housing and a chute of the handheld compound tester of FIG. 11, in accordance with some configurations.
Figure 17:
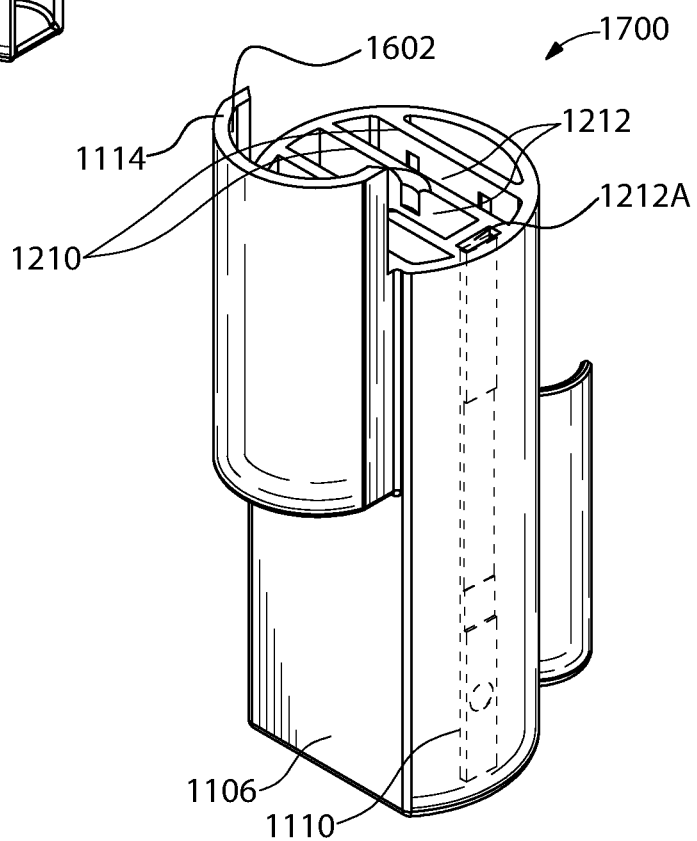

Referring now to FIGS. 16-17, different perspective views 1600, 1700 of an assembly of the housing 1106 and the chute 1114 of the handheld compound tester 1100 are illustrated, in accordance with some configurations of the present disclosure. As shown in FIG. 16, the housing 1106 may include the plurality of vertical walls 1210 defining the plurality of compartments 1212 in the housing. Further, the test strip 1110 (shown in dotted profile) may be disposed within the test compartment 1212A of the housing 1106. As will be appreciated, this design of the housing 1106 allows for an easy assembly of the test strip 1110 with the housing 1106 by simply sliding in the test strip 1110 inside the test compartment 1212A.

For example, in some configurations, as shown in FIG. 16, the cut-out window 1112 may be formed as a cut-out opening in the housing 1106. Further, a transparent sheet may be provided over this cut-out opening to fluidically seal the cut-out opening to thereby prevent any leakage of the liquid or the mixture from the housing 1106. In alternate configurations, as shown in FIG. 17, the entire housing 1106 may be transparent. As such, the test strip 1110 positioned inside the housing 1106 may be visible to the user through the housing 1106.

Further, as shown in FIGS. 16-17, the chute 1114 may include an open top face 1602, such that segments of the tablet 1202 from the chute 1114 can be retrieved by the user via the open top face 1602. In some configurations (as shown in the FIG. 15), the lid 1104 may be shaped such so as to cover the open top face 1602 of the chute 1114 in the closed position of the lid 1104.

Referring once again to FIG. 12, the handheld compound tester 1100 may further include the liquid ampoule 1116 from where the liquid supplied to the sampling chamber 1102 may be retrieved. The liquid ampoule 1116 may store a predetermined volume of the liquid. The liquid ampoule 1116 may be detachably attached to the handheld compound tester 1100, in particularly to the housing 1106 via the holder 1120. The liquid ampoule 1116 may include the dispensing head 1118 to dispense the liquid inside the liquid ampoule 1116. This is further explained in conjunction with FIGS. 18A-18B.

Figure 18A:
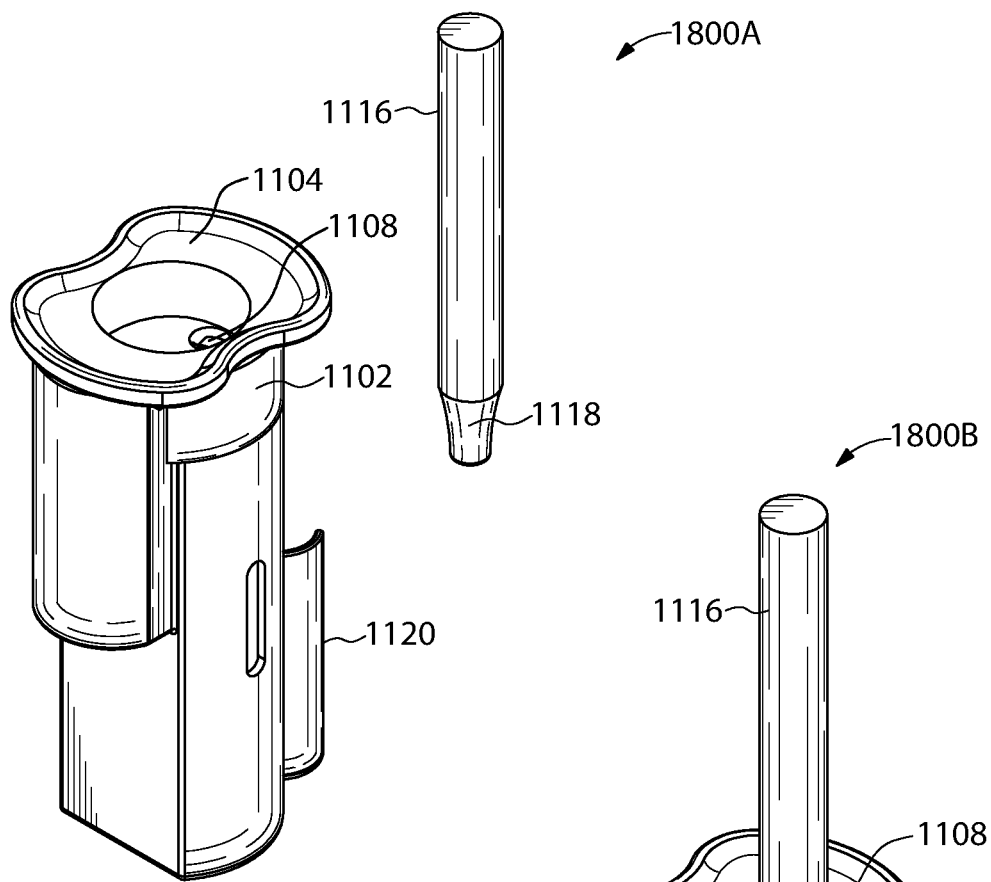
FIGS. 18A-18B illustrate perspectives views of the handheld compound tester including a liquid ampoule, in accordance with some configurations.
Figure 18B:
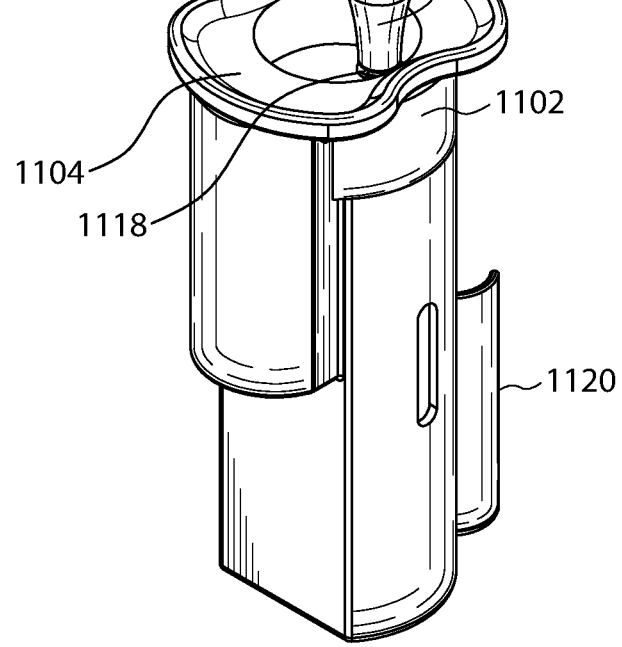

Referring now to FIGS. 18A-18B, perspectives views 1800A, 1800B of the handheld compound tester 1100 including the liquid ampoule 1116 are illustrated, in accordance with some configurations of the present disclosure. As shown in FIG. 18A, the liquid ampoule 1116 may be configured to be disengaged from the housing 1106 of the handheld compound tester 1100. The liquid ampoule 1116 may include the dispensing head 1118. Further, as shown in FIG. 18B, the dispensing head 1118 of the liquid ampoule 1116 may be configured to fit into the opening 1108 of the lid 1104 to supply the liquid to the sampling chamber 1102. In some configurations, the liquid ampoule 1116 may be squeezable, such that, upon being squeezed, the liquid inside the liquid ampoule 1116 is pushed out via the dispensing head 1118 and supplied to the sampling chamber 1102. Alternately, the liquid ampoule 1116 may include a piston (not shown in FIGS. 18A-18B) and a cylinder assembly with the piston being configured to be pushed inside to push water from the cylinder into the sampling chamber 1102.

Referring now to FIGS. 19A-19C, different views of the handheld compound tester 1100 are illustrated, in accordance with some configurations of the present disclosure. FIG. 19A illustrates a side view of the handheld compound tester 1100. FIG. 19B illustrates a first sectional view of the handheld compound tester 1100 of FIG. 19A along a section line A-A' in a first configuration. FIG. 19C illustrates a sectional view of the handheld compound tester 1100 of FIG. 19A along the section line A-A' in a second configuration. The first configuration of the handheld compound tester 1100 may correspond to the housing 1106 being empty, and the second configuration of the handheld compound tester 1100 may correspond to the housing 1106 having received the mixture from the sampling chamber 1102.

As shown in FIG. 19B, in the first configuration, the housing 1106 of the handheld compound tester 1100 may not include any mixture of the liquid and the segments of the tablet 1202. As such, the plurality of compartments 1212 defined inside the housing 1106 may be empty. As will be understood, the test strip 1110 (not shown in FIGS. 19A-19C) may not provide any indication about the presence of the compound within the mixture.

In the second configuration, as shown in FIG. 19C, the housing 1106 of the handheld compound tester 1100 may include mixture 1902 of the liquid and the segments of the tablet 1202. As such, the plurality of compartments 1212 defined inside the housing 1106 may include the mixture 1902. Further, the mixture 1902 in the test compartment may contact the test strip 1110 from below, and owing to the capillary action, the mixture 1902 may rise above along the length of the test strip 1110. Further, the mixture 1902, depending upon the presence of the target compound in the mixture 1902, may cause the test strip 1110 to indicate the presence of the compound in the mixture 1902. It should be noted that the test strip 1110 (not shown in FIGS. 19A-19C) may not provide the indication for a specific period of time, for example, one or two minutes. This is because the chemical reaction (which is responsible for generating that indication on the test strip) of the compound with the test strip may take that specific period of time to complete.

As already explained above, the test compartment 1212A of the housing 1106 may be configured to receive a predefined maximum volume of the liquid mixture which may contact a maximum predefined length of the test strip 1110 from a bottom end of the test strip 1110. The housing 1106 may be configured to evenly distribute the liquid mixture entering in the housing 1106 among the plurality of compartments 1212 including the test compartment 1212A. As shown in FIG. 19C, the liquid mixture (shown in solid profile in FIG. 19C) may be evenly distributed in the plurality of compartments 1212 including the test compartment 1212A. This even distribution of the mixture in the plurality of compartments 1212 may be provisioned by the hole towards the bottom end of the plurality of vertical walls 1210 that fluidically couples the plurality of compartments 1212 with each other.

Figure 20:
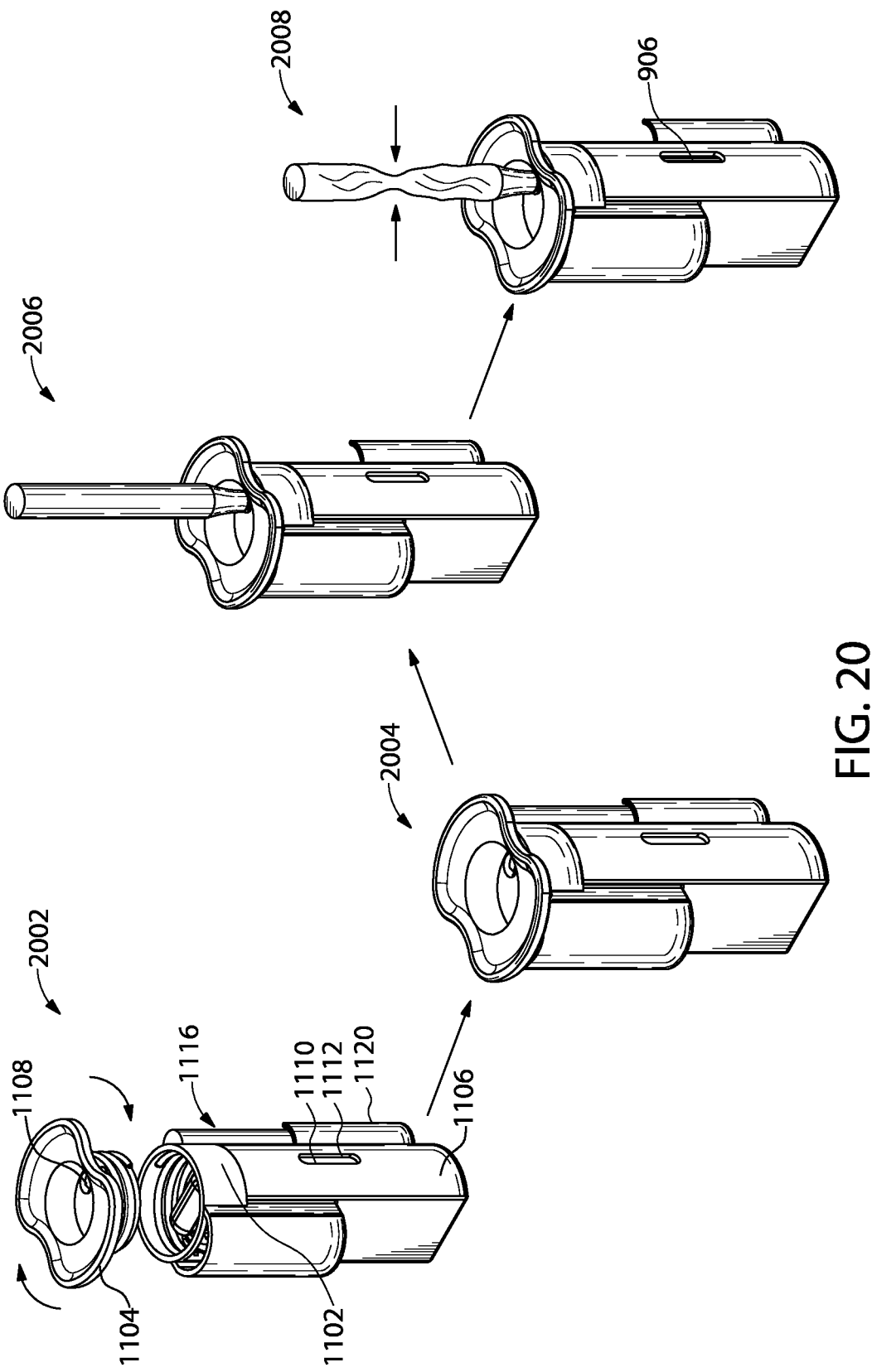
FIG. 20 is a process flow diagram of a process of processing and detecting presence of a target compound in a tablet, in accordance with some configurations.
Figure 21:
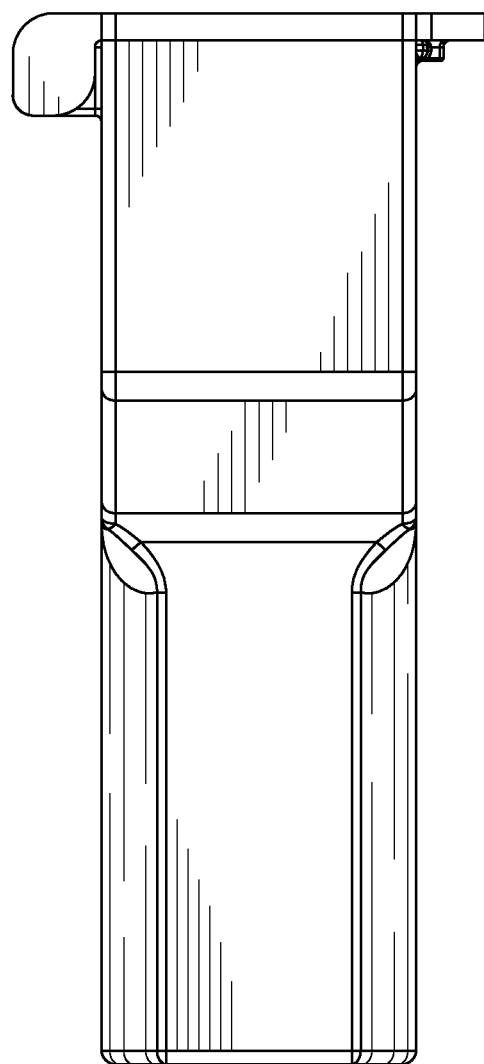
FIGS. 21-26 illustrate different views (i.e., a left side view, a right side view, a front view, a rear view, a top view, and a bottom view, respectively) of an ornamental design of the handheld compound tester of FIG. 1, in closed position of the lid in accordance with some configurations.
Figure 22:
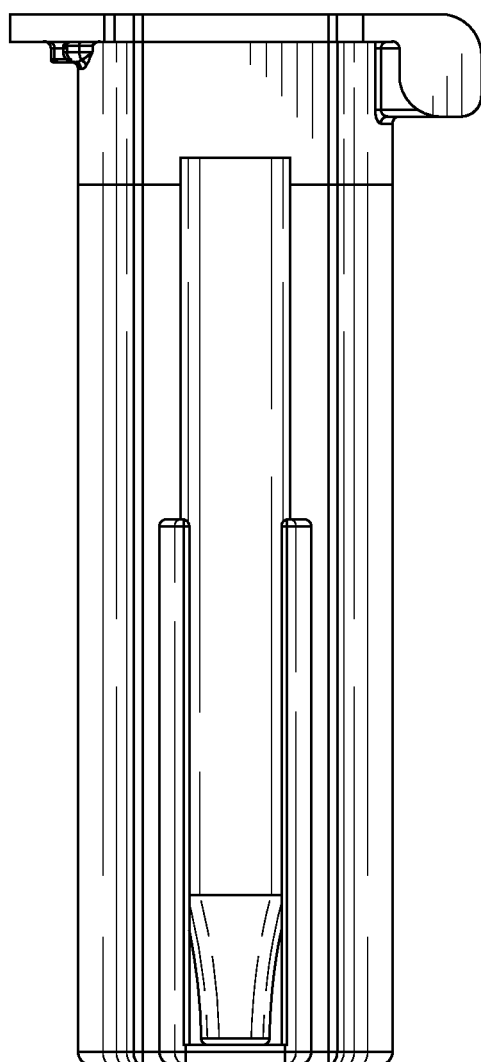
Figure 23:
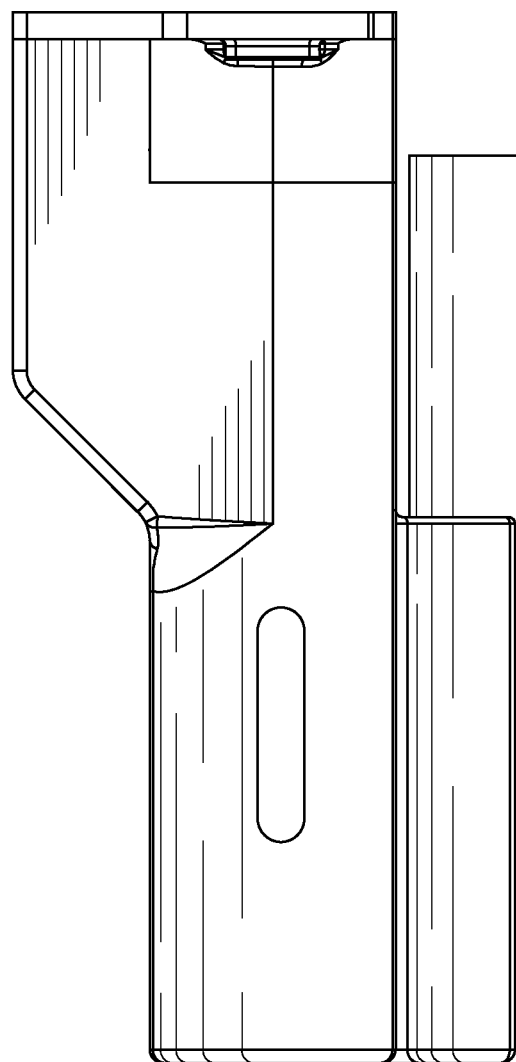
Figure 24:
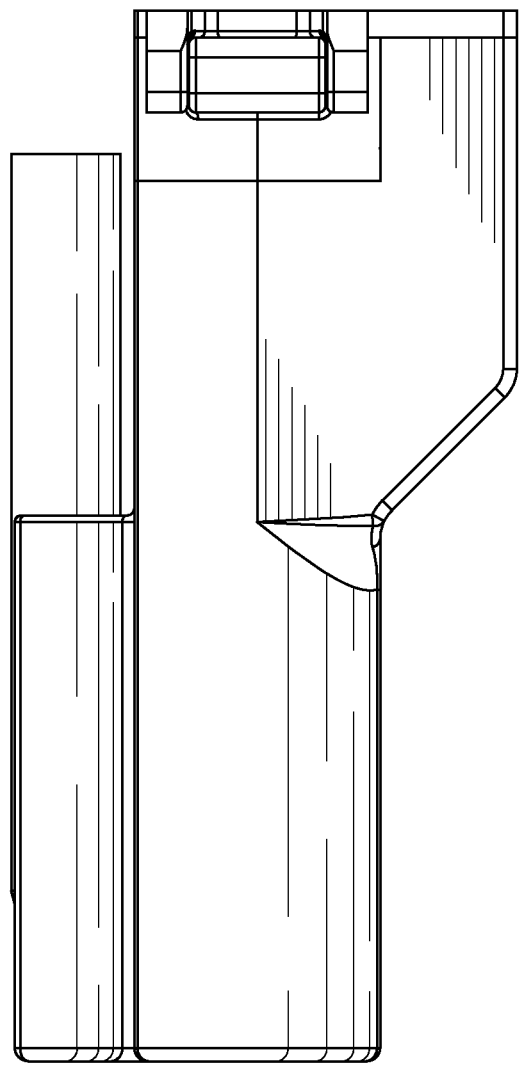
Figure 25:
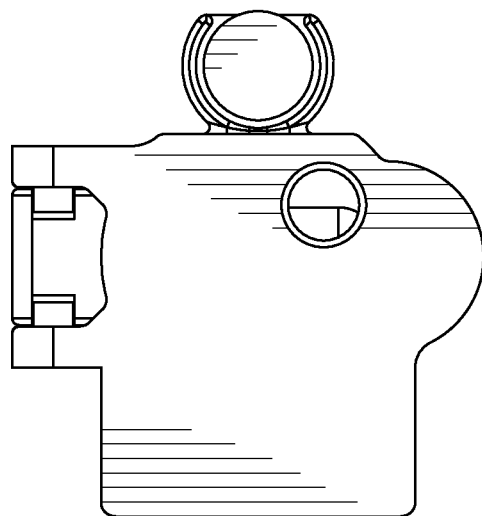
Figure 26:
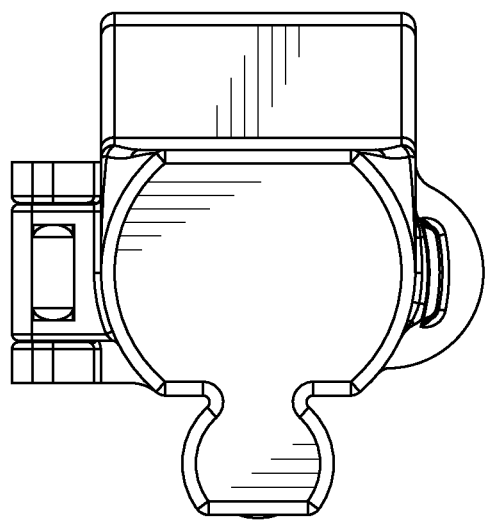
Figure 27:
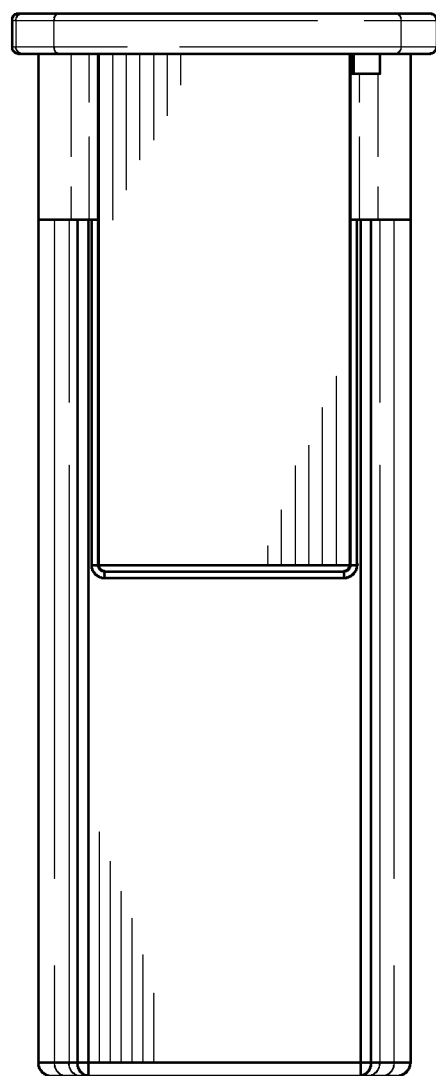
FIGS. 27-32 illustrate different views (i.e., a left side view, a right side view, a front view, a rear view, a top view, and a bottom view, respectively) of an ornamental design of the handheld compound tester of FIG. 11, in closed position of the lid, in accordance with some configurations.
Figure 28:
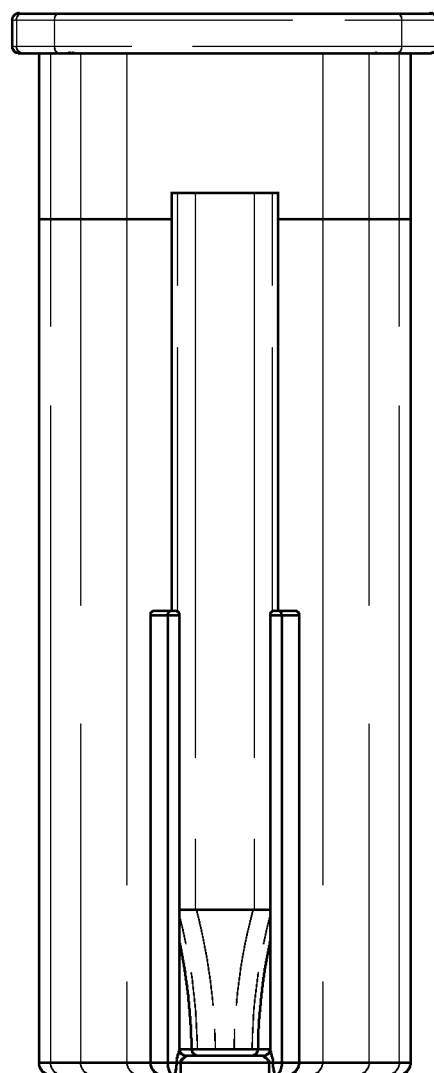
Figure 29:
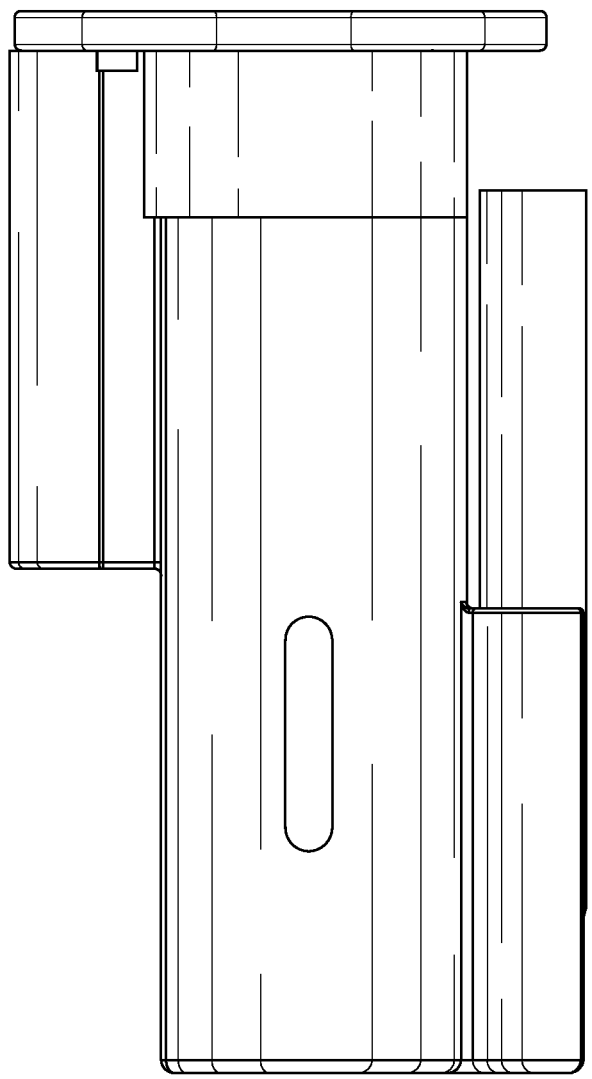
Figure 30:
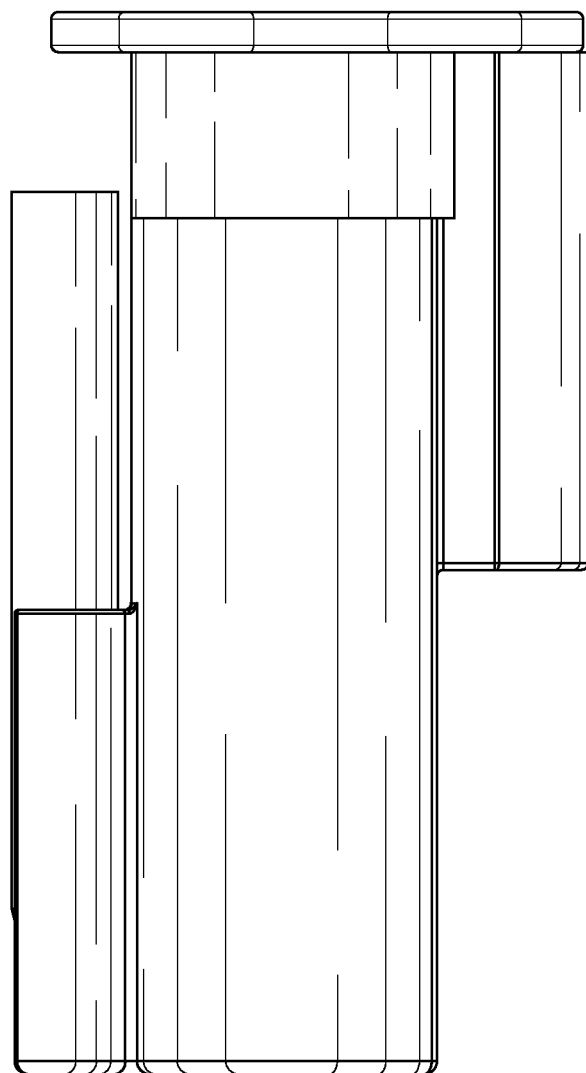
Figure 31:
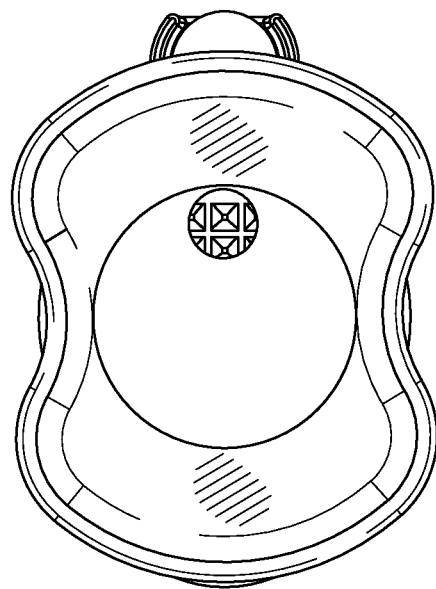
Figure 32:
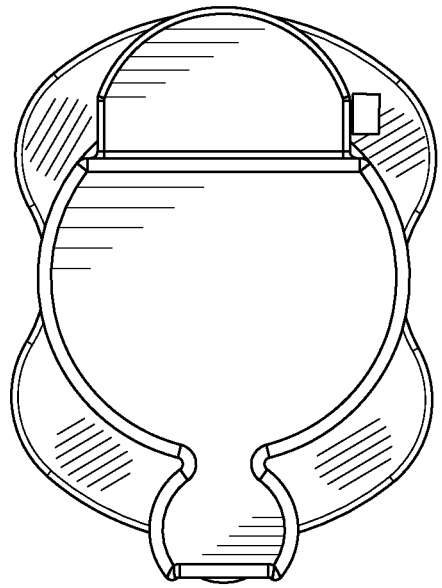

Referring now to FIG. 20, a process flow diagram of a process 2000 of processing and detecting presence of the target compound in the tablet 1202 is illustrated, in accordance with some configurations of the present disclosure. At step 2002, the handheld compound tester 1100 for processing and detecting the presence of the compound in the tablet 1202 may be provided. As explained above with reference to FIGS. 1-9, the handheld compound tester 1100 may include the sampling chamber 1102. The sampling chamber 1102 may include the at least one inner boundary wall 1216, and the bottom surface 1218 which may include the bottom hole 1220. The handheld compound tester 1100 may further include the lid 1104 which may be couplable with the sampling chamber 1102 via thread coupling. The lid 1104 may include the top side 1104A and the bottom side 1104B. The lid 1104 may further include the opening 1108 to provide a supply of the liquid into the sampling chamber

1102. The lid 1104 may be configured to transition between the open position and the closed position. In the open position, the lid 1104 is uncoupled from the sampling chamber 1102. In the closed position, the lid 1104 is coupled with the sampling chamber 1102 to thereby define an inner space along with the at least one inner boundary wall 1216 and the bottom surface 1218. The handheld compound tester 1100 may further include housing 1106 defined vertically below the sampling chamber 1102. The housing may be fluidically coupled with the sampling chamber 1102 via the bottom hole 1220. The test strip 1110 may be disposed within the housing 1106.

Further, in some configurations, the handheld compound tester 1100 may include the chute 1114 defined adjacent to the sampling chamber 1102. The chute 1114 may be configured to receive some segments of the tablet 1202 created upon cutting of the tablet 1202 during the transition of the lid 1104 from the open position to the closed position. In some configurations, the at least one inner boundary wall 1215 (not shown) may include side opening 1214, such that the chute 1114 may receive the remaining segments of the tablet 1202 via the side opening 1214. In some configurations, the lid 1104 may include the threaded head 1206A projecting substantially perpendicular to the bottom side 1104B of the lid 1104. In some configurations, the lid 1104 may further include at least one projection 1402 projecting perpendicular to the bottom side 1104B of the lid 1104. The at least one projection 1402 may be configured to contact and cut the tablet 1202 inside the sampling chamber 1102 during the transition of the lid 1104 from the open position to the closed position. In some configurations, the bottom surface 1218 of the sampling chamber 1102 may include the plurality of spikes 1502 pointing towards the bottom side 1104B of the lid 1104.

In some configurations, the handheld compound tester 1100 may include the liquid ampoule 1116 which may store a predetermined volume of liquid. The liquid ampoule 1116 may be configured to be detachably attached to the housing 1106. The liquid ampoule 1116 may include the dispensing head 1118 to dispense the liquid stored inside the liquid ampoule 1116, such that the dispensing head 1118 is configured to fit into the opening 1108 of the lid 1104.

Further, at step 2002, in the open position, the lid 1104 may be uncoupled from the sampling chamber 1102. Furthermore, at step 2002, the tablet 1202 may be positioned inside the sampling chamber 1102 with the lid 1104 in the open position. It should be noted that at the step 2002, the liquid ampoule 1116 may be attached to the housing 1106, i.e. intact within the holder 1120. Once the tablet 1202 is positioned inside the sampling chamber 1102, the lid 1104 may be transitioned from the open position to the closed position.

In some configurations, the housing 1106 may include the plurality of vertical walls 1210 defining a plurality of compartments 1212 including the test compartment 1212A. The test compartment 1212A may be fluidically coupled with the sampling chamber 1102 via the bottom hole 1220 and configured to receive the mixture 1902 of the liquid and the segment of the tablet 1202 from the sampling chamber 1102. Further, the test compartment 1212A may be configured to receive a maximum predefined volume of the mixture. The test strip 1110 may be disposed within the test compartment 1212A. Further, the maximum predefined volume of the mixture may contact a maximum predefined length of the test strip 1110 from a bottom end of the test strip.

At step 2004, the lid 1104 may be transitioned in the closed position, i.e., the transitioned of the lid 1104 from the open position to the closed position may be complete. The transition may take place by rotating the lid 1104 relative to the sampling chamber 1102 allowing the threaded head 1206A to engage with the threaded portion 1206B of the sampling chamber 1102. In other words, the transition comprises rotating the lid about an axis perpendicular to the bottom side 1104B of the lid 1104. As a result, the lid 1104 may be coupled with the sampling chamber 1102 to thereby define an inner space along with the at least one inner boundary wall 1216 (not shown) and the bottom surface 1218. Further, at the step 2004, the liquid ampoule 1116 may still be attached to the housing 1106, i.e. intact within the holder 1120.

It should be noted that during the transition from the open to the closed position, the lid 1104 may cut the tablet 1202 inside the sampling chamber 1102. The tablet 1202 may be cut to generate a plurality of segments of the tablet. As will be understood, the cutting of the tablet 1202 may be occur by way of the tablet 1202 being sandwiched between the at least one projection 1402 and the plurality of spikes 1502. Further, during the transition of the lid 1104 from the open position to the closed position, the threaded head 1206A may extend over the side opening 1214 to shut the side opening 1214. As a result, the threaded head 1206A may block passage of the liquid or the mixture 1902 from the sampling chamber 1102 to chute 1114 when the liquid is added to the sampling chamber 1102 in the subsequent step.

At step 2006, once the lid 1104 has transitioned into the closed position, the liquid ampoule 1116 may be detached from the holder 1120 and further fitted to the opening 1108 of the lid 1104. In particular, the dispensing head 1118 of the lid 1104 may be fit into the opening 1108 of the lid 1104 to dispense the liquid stored inside the liquid ampoule 1116. In some configurations, the dispensing head 1118 may have a circular profile similar to a circular profile of the opening 1108 to therefore allow the dispensing head 1118 to fit in the opening 1108. Further, in some configurations, the dispensing head 1118 may be made from a flexible material, for example a plastic, or a rubber, etc. which may further aid in the fitting of the dispensing head 1118 in the opening 1108.

At step 2008, the liquid may be supplied from liquid ampoule 1116 to the sampling chamber 1102 to create the mixture 1902 of the liquid and segments of the tablet 1202 already present inside the sampling chamber 1102. In some configurations, the liquid ampoule 1116 may be squeezable. Therefore, in order to supply the liquid from the liquid ampoule 1116 to the sampling chamber 1102, the liquid ampoule 1116 may be squeezed, as shown in FIG. 20. For example, the liquid ampoule 1116 may be squeezed manually by pressing the liquid ampoule 1116 between an index finger and a thumb of the user. Upon being squeezed, the liquid ampoule 1116 may be configured to supply the liquid stored inside the liquid ampoule 1116 to the sampling chamber 1102 via the dispensing head 1118. Once the liquid is received inside the sampling chamber 1102, the mixture 1902 of the liquid and the segments of the tablet 1202 already present inside the sampling chamber 1102 may be created.

The mixture 1902 may then pass to the test compartment 1212A of the housing 1106 via the bottom hole 1220 of the sampling chamber 1102. The test compartment 1212A may be configured to receive a maximum predefined volume of the mixture 1902. As the test strip 1110 is disposed within the test compartment 1212A, the maximum predefined volume of the mixture may contact a maximum predefined length of the test strip 1110 from a bottom end of the test strip 1110. Upon contacting, the test strip 1110 may indicate a presence of the target compound within the mixture 1902.

As such, further at step 2008, the test strip 1110 may be viewed by the user. To this end, in some configurations, the housing 1106 may include the cut-out window 1112 located along the test compartment 1212A and the test strip 1110 may be positioned adjacent to the cut-out window 1112, such that at least a portion of the test strip 1110 is visible to the user via the cut-out window 1112. Alternately, the entire housing 1106 may be transparent, to thereby allow at least a portion of the test strip 1110 to be visible to the user through the transparent housing1106.

Additionally, the unused segments of the tablet 1202 that are moved into the chute 1114 may be retrieved by the user. To this end, in some configurations, the chute 1114 may include the open top face 1602, such that segments of the tablet 1202 from the chute 1114 can be retrieved by the user via the open top face 1602. As mentioned earlier, the lid 1104 may be shaped to cover the open top face 1602 of the chute 1114 in the closed position of the lid 1104. Therefore, in order to retrieve the unused segments of the tablet 1202 from the chute 1114, first, the lid 1104 may be removed from the open top face 1602, to allow access to the chute 1114 via the open top face 1602.

As will be understood, if the test strip 1110 indicates a positive presence of the compound (e.g. fentanyl) inside the mixture 1902 (i.e. inside the tablet 1202), the tablet 1202 may be considered unsafe. As such, upon retrieving the unused segments from the chute 1114, the unused segments of the tablet may be discarded or reported to a drug authority. However, if the test strip 1110 indicates a negative presence of the target compound inside the mixture and the tablet 1202 (i.e. the target compound is absent), the tablet 1202 may be considered as safe, and therefore deemed fit for consumption. Since only a small percentage of segments of the tablet 1202 are left inside the sampling chamber 1102 for detecting the compound and majority of the tablet segments are moved to the chute 1114, therefore, majority of the tablet can be retrieved and can be consumed by the user.

It is intended that the disclosure and examples be considered as exemplary only, with a true scope and spirit of disclosed configurations being indicated by the following claims and amendments made thereto in the original application, divisional applications, continuations application, and/or foreign applications.

What is claimed is:

1. A handheld device for processing a tablet, the handheld device comprising:
    a sampling chamber configured to receive the tablet, wherein the sampling chamber comprises:
        at least one inner boundary wall;
        a side opening defined on the at least one inner boundary wall; and
        a bottom surface comprising;
            a bottom hole;
    a lid configured to be couplable with the sampling chamber, wherein the lid comprises:
        a top side;
        a bottom side;
        a top opening across the top side and the bottom side to provide a supply of a liquid into the sampling chamber;
        a partition wall projecting substantially perpendicular to the bottom side of the lid;
        an open position;
            wherein, in the open position, the lid is partially or completely detached from the sampling chamber;
        a closed position different than the open position;
            wherein, in the closed position, the lid is coupled with the sampling chamber to thereby define an inner space along with the at least one inner boundary wall and the bottom surface;
        a dividing position different than the open position and the closed position;
            wherein, in the dividing position, the partition wall of the lid is configured to divide the tablet into a first portion and a second portion inside the sampling chamber;
        wherein in the closed position of the lid, the supply of the liquid is received into the sampling chamber via the top opening, to create a mixture of the liquid and the first portion of the tablet; and
        wherein the partition wall is further configured to extend over the side opening to block passage of the mixture of the liquid and the first portion of the tablet, outside from the sampling chamber, in the closed position of the lid; and
    a housing adjoining the sampling chamber;
        wherein the housing is fluidically coupled with the sampling chamber via the bottom hole to receive the mixture of the liquid and the first portion of the tablet, and
        wherein the second portion of the tablet is removed from the sampling chamber, via the side opening.

2. The handheld device of claim 1 further comprising:
    a chute defined adjacent to the sampling chamber;
        wherein the chute is configured to receive the second portion of the tablet via the side opening.

3. The handheld device of claim 1, wherein the tablet is one of:
    a solid;
    a paste;
    a liquid; and
    a powder sample.

4. The handheld device of claim 1, wherein the lid further comprises:
    at least one projection projecting perpendicular to the bottom side of the lid;
        wherein the at least one projection is configured to contact and cut the tablet inside the sampling chamber during transition of the lid from the open position to the closed position, when the tablet is the tablet.

5. The handheld device of claim 4, wherein the bottom surface comprises:
    a plurality of spikes pointing towards the bottom side of the lid;
        wherein during transition of the lid from the open position to the closed position, the tablet is sandwiched between the plurality of spikes and the at least one projection.

6. The handheld device of claim 1, wherein the housing further comprises:
    a plurality of vertical walls defining a plurality of compartments;
        wherein a test compartment of the plurality of compartments is fluidically coupled with the sampling chamber via the bottom hole to receive the mixture of the liquid and the second portion of the tablet.

7. The handheld device of claim 1, wherein the lid is couplable with the sampling chamber or the housing via a hinged coupling.

8. The handheld device of claim 1, further comprising:
a liquid ampoule configured to store a predetermined volume of liquid;
wherein the liquid ampoule is configured to be detachably attached to the housing.

9. The handheld device of claim 8, wherein the liquid ampoule comprises:
a dispensing head to dispense the liquid stored inside the liquid ampoule;
wherein the dispensing head is configured to fit into the top opening of the lid to supply the liquid inside the sampling chamber.

10. The handheld device of claim 9,
wherein the liquid ampoule is squeezable; and
wherein, upon being squeezed, the liquid ampoule is configured to supply the liquid stored inside the liquid ampoule to the sampling chamber via the dispensing head.

11. The handheld device of claim 1,
wherein a test strip is disposed within the housing;
wherein the test strip is configured to contact the mixture of the liquid and the first portion of the tablet;
wherein, upon contacting, the test strip is further configured to indicate a presence of a compound in the mixture; and
wherein at least a portion of the test strip is configured to be visible to a user.

12. A method of processing a tablet, the method comprising:
providing a handheld device for processing the tablet, wherein the handheld device comprises:
a sampling chamber comprising:
at least one inner boundary wall; and
a bottom surface comprising;
a bottom hole; and
a lid configure to be couplable with the sampling chamber, the lid comprising:
a top side;
a bottom side; and
a top opening to provide a supply of liquid into the sampling chamber;
wherein the lid is configured to transition between an open position and a closed position;
wherein in the open position, the lid is uncoupled from the sampling chamber; and
wherein in the closed position, the lid is coupled with the sampling chamber to thereby define an inner space along with the at least one inner boundary wall and the bottom surface; and
a housing defined vertically below the sampling chamber;
wherein the housing is fluidically coupled with the sampling chamber via the bottom hole;
positioning the tablet inside the sampling chamber, in the open position of the lid;
transitioning the lid from the open position to the closed position to divide the tablet into a first portion of the tablet and a second portion of the tablet, and to obtain the closed position of the lid;
supplying the liquid to the sampling chamber to create a mixture of the liquid and the first portion of the tablet; and
wherein, upon creation of the mixture, the mixture is received by the housing from the sampling chamber via the bottom hole.

13. The method of claim 12 further comprising:
contacting the mixture with a test strip in the housing;
wherein, upon contacting, the test strip is configured to indicate a presence of a compound within the mixture.

14. The method of claim 13, wherein the housing further comprises:
a plurality of vertical walls defining a plurality of compartments;
wherein a test compartment of the plurality of compartments is fluidically coupled with the sampling chamber via the bottom hole and configured to receive the mixture of the liquid and the first portion of the tablet;
wherein the test compartment is further configured to receive a maximum predefined volume of the mixture;
wherein the test strip is configured to be disposed within the test compartment; and
wherein the maximum predefined volume of the mixture is to contact a maximum predefined length of the test strip from a bottom end of the test strip.

15. The method of claim 12 further comprising:
receiving the second portion of the tablet in a chute, from the sampling chamber via a side opening defined on the at least one inner boundary wall of the sampling chamber,
wherein the chute is defined adjacent to the sampling chamber on the handheld device; and
wherein the chute comprises:
an open top face; and
retrieving the second portion of the tablet from the chute via the open top face.

16. The method of claim 12,
wherein the lid is couplable with the sampling chamber via a hinged coupling; and
wherein transitioning the lid from the open position to the closed position comprises rotating the lid about the hinged coupling.

17. The method of claim 12, wherein supplying the liquid to the sampling chamber comprises:
detaching a liquid ampoule from the handheld device;
fitting a dispensing head associated with the liquid ampoule into the top opening of the lid; and
upon fitting, squeezing the liquid ampoule to dispense the liquid into the sampling chamber.

18. A handheld device for processing a tablet, the handheld device comprising:
a sampling chamber comprising:
at least one inner boundary wall comprising:
a side opening; and
a bottom surface;
a lid configured to be couplable with the sampling chamber, wherein the lid comprises:
a top side;
a bottom side;
a top opening formed between the top side and the bottom side to provide a pathway for a liquid to travel into the sampling chamber;
a partition wall projecting substantially perpendicular to the bottom side of the lid;
wherein the lid is configured to transition between an open position and a closed position, wherein,
in the open position, the lid is uncoupled from the sampling chamber;
in the closed position, the lid is coupled with the sampling chamber to thereby define an inner space along with the at least one inner boundary wall and the bottom surface;

wherein the partition wall of the lid is configured to divide the tablet into a first portion and a second portion inside the sampling chamber during transition of the lid from the open position to the closed position;

wherein the second portion of the tablet is removed from the sampling chamber via the side opening; and wherein in the closed position of the lid,
- the liquid is received into the sampling chamber via the top opening, to create a mixture of the liquid and the first portion of the tablet; and
- the partition wall is configured to extend over the side opening to block passage of the mixture of the liquid and the first portion of the tablet outside from the sampling chamber.

19. The handheld device of claim 18 and further comprising:
   - a chute attached to the sampling chamber; and
   - wherein the chute is configured to receive the second portion of the tablet, via the side opening.

20. The handheld device of claim 18 and further comprising:
   - a housing attached below the sampling chamber;
   - a bottom hole formed in the bottom surface of the sampling chamber;
   - wherein the housing is fluidically coupled to the sampling chamber via the bottom hole and configured to receive the mixture of the liquid and the first portion of the tablet; and
   - a test strip disposed within the housing;
     - wherein the test strip is configured to contact the mixture;
     - wherein, upon contacting, the test strip is further configured to indicate a presence of a compound in the mixture; and
     - wherein the test strip is further configured to be visible to a user through the housing.

* * * * *